US005559025A

United States Patent [19]

Ahorn et al.

[11] Patent Number: 5,559,025
[45] Date of Patent: Sep. 24, 1996

[54] EXPRESSION OF MATURE PROTEINASE 2A, THE PARTIAL PURIFICATION THEREOF AND PREPARATION OF SUBSTRATES HAVING AN INHIBITORY EFFECT

[75] Inventors: Horst Ahorn, Weigelsdorf; Ingrid Maurer-Fogy; Wolfgang Sommergruber, both of Vienna; Andreas Zöphel, Neulengbach; Dieter Blaas, Vienna; Ernst Küchler, Vienna; Hans-Dieter Liebig, Vienna; Timothy Skern, Vienna all of Austria

[73] Assignee: Boehringer Ingelheim International GmbH, Ingelheim, Germany

[21] Appl. No.: 320,373

[22] Filed: Oct. 11, 1994

Related U.S. Application Data

[63] Continuation of Ser. No. 971,619, Nov. 6, 1992, abandoned.

[30] Foreign Application Priority Data

Nov. 6, 1991 [DE] Germany .......................... 41 36 443.0

[51] Int. Cl.$^6$ .............................. C12N 1/21; C12N 15/70
[52] U.S. Cl. .................. 435/252.33; 435/320.1; 435/252.3; 435/172.3; 435/219; 435/212; 536/23.72; 536/23.2; 935/9; 935/14; 935/22; 935/29; 935/72; 935/73
[58] Field of Search .............................. 435/320.1, 252.3, 435/252.33, 172.3, 219, 212, 849; 536/23.72, 23.2; 935/9, 14, 22, 29, 66, 72, 73

[56] References Cited

U.S. PATENT DOCUMENTS 5,149,783   9/1992   Sommergruber et al. ............... 530/326

FOREIGN PATENT DOCUMENTS

| 599895 | 8/1990 | Australia . |
|---|---|---|
| 0196921 | 10/1986 | European Pat. Off. . |
| 0321973 | 6/1989 | European Pat. Off. . |
| 3505148 | 10/1986 | Germany . |
| 56-086142 | 7/1981 | Japan . |
| WO86/04901 | 8/1986 | WIPO . |
| WO91/00348 | 1/1991 | WIPO . |

OTHER PUBLICATIONS

*Stedman's Medical Dictionary* 25th Edition, 1990, Hensyl et al.(eds.), Williams & Wilkins., Baltimore, MD. p. 792.

Agol, V.I., "Structure, translation, and replication of picornaviral genomes", *Prog. Med. Virol.*26:119–157 (1980).

Butterworth, B. E., "A comparison of the virus-specific polypeptides of encephalomyocarditis virus, human rhinovirus", *Virology* 56:439–453 (1973).

Callahan, P. L. et al., "Molecular cloning and complete sequence determination of RNA genome of human rhinovirus type 14", *Proc. Natl. Acad. Sci. USA* 82:732–736 (Feb. 1985).

Duechler, M. et al., "Evolutionary relationships within the human rhinovirus genus: comparison of sterotypes 89, 2, and 14", *Proc. Natl. Acad. Sci. USA* 84:2605–2609 (May 1987).

Hanecek, R. et al., "Proteolytic processing of poliovirus polypeptides: antibodies to polypeptides P3–7c inhibit cleavage at glutamine–glycine pairs", *Proc. Natl. Acad. Sci. USA* 79:3973–3977 (Jul. 1982).

Hughes, P. J. et al., "The nucleotide sequence of human rhinovirus 1B: molecular relatonships within the rhinovirus genus", *J. Gen. Virol.*69:49–58 (1988).

König, H. and Rosenwirth, B., "Purification and partial characterization of poliovirus protease 2A by means of a functional assay", *J. Virol.* 62(4):1243–1250 (Apr. 1988).

Kowalski, H. et al., "Cleavage site between VP1 and P2A of human rhinovirus is different in stereotypes 2 and 14", *J. Gen. Virol.* 68:3197–3200 (1987).

Kräusslich, H. G. and Wimmer, E., "Viral proteinases", *Ann. Rev. Biochem.* 57:701–754 (1988).

Kräusslich, H. G. et al., "Poliovirus proteinase 2A induces cleavage of eucaryotic initiation factor 4F polypeptide p220", *J. Virol.* 61(9):2711–2718 (Sep. 1987).

Lee, C. K. and Wimmer, E., "Proteolytic processing of poliovirus polyprotein: elimination of $2A^{pro}$–mediated, alternative cleavage of polypeptide 3CD by in Vitro mutagenesis", *Virol.*166:405–414 (1988).

Lloyd, R. E. et al., "Cleavage of the cap binding protein complex polypeptide p220 is not effected by the second poliovirus protease 2A", *Virol.* 150:299–303 (1986).

Lloyd, R. E. et al., "restriction of translation of capped mRNA in vitro as a model for poliovirus–induced inhibition of host cell protein synthesis: relationship to p220 cleavage", *J. Virol.* 61(8):2480–2488 (Aug. 1987).

McLean, C. and Rueckert, R. R., "Picornaviral gene order: comparison of a rhinovirus with a cardiovirus", *J. Virol. 11(2):341–344 (Feb. 1973)*.

McLean, C. et al., "Evidence of ambiguous processing and selective degradation in the noncapsid proteins of rhinovirus 1A", *J. Virol.* 19(3):903–914 (Sep. 1976).

Nicklin, M. J. H., "Poliovirus polypeptide precursors: expression *in vitro* and processing by exogenous 3C and 2A proteinases", *Proc. Natl. Acad. Sci. USA*, 84:4002–4006 (Jun. 1987).

Palmenberg, A. C., "Chapter 13–Sequence alignments of picornaviral capsid proteins", *Molecular Aspects of Picornavirus Infection and Detection,* Semler and Ehrenfeld, eds., Washington, D.C., American Society for Microbiology, 211–241 (1989).

Palmenberg, A. C., "Picornaviral processing: some new ideas", *j. Cell.*Biochem. 33:191–198 (1987).

Putnak, J. R. and Phillips, B. A., "Picornaviral structure and assembly", *Microbiol. Rev.* 45(2):287–315 (Jun. 1981).

(List continued on next page.)

*Primary Examiner*—Christopher S. F. Low
*Attorney, Agent, or Firm*—Sterne, Kessler, Goldstein & Fox P.L.L.C.

[57] ABSTRACT

The invention relates to the expression of mature HRV proteinase 2A, the partial purification thereof and the preparation of substrates having an inhibitory effect.

2 Claims, 15 Drawing Sheets

OTHER PUBLICATIONS

Skern, T. et al., "Human rhinovirus 2: complete nucleotide sequence and proteolytic processing signals in the capsid protein region", *Nucleic Acids Res.* 13(6):2111–2126 (1985).

Sommergruber, W. et al., "Polypeptide 2A of human rhinovirus type 2: identification as a protease and characterization by mutational analysis", *Virology* 169:68–77 (1989).

Stanway et al., "the nucleotide sequence of poliovirus type 3 leon 12 $a_1b$: comparison with poliovirus type 1", *Nucl. Acids Res.* 11(16): 5629–5643 (1983).

Stanway, G. et al., "The complete nucleotide sequence of a common cold virus: human rhinovirus 14", *Nucleic Acids Res.* 12(20):7859–7875 (1984.

Stanway, G., "Structure, function, and evolution of picornaviruses", *J. Gen. Virol.* 71:2483–2501 (1990).

Billich et al., Synthetic Peptides as Substrates and Inhibitors of Human Immune Deficiency Virus–1 Protease, *Journal of Biological Chemistry* 263(34):17905–17908 (1988).

English abstract of Japanese Patent document JP–A–56 086 142 (Reference AL1), Derwent abstract No. 81–63212D.

Clonetech Catalog, 1991–1992, p. 132, Palo Alto, CA.

FIG. 5

| Inhibitor Class | Inhibitor | $IC_{50}$ (µmol/l) |
|---|---|---|
| Metallo Protease | Epiamastatin<br>Foroxymithin<br>Phosphoramidon<br>Amastatin<br>Bestatin<br>Epibestatin<br>EGTA<br>EDTA<br>1,10 Phenanthroline | -<br>-<br>-<br>-<br>-<br>-<br>-<br>16 500<br>3 200 |
| Asp Protease | NLE-Sta-Ala-Ala<br>Pepstatin | -<br>- |
| Ser Protease | 3,4-dichloro-isocoumarin<br>Elastatinal<br>APMSF<br>TLCK<br>TPCK<br>PMSF | 1430<br>55<br>-<br>80<br>1300<br>1200 (±500)* |
| Cys Protease | E-64<br>Iodacetamide<br>NEM | -<br>90<br>28 |
| Cys/Ser Protease | Antipain<br>Leupeptin<br>Chymostatin<br>pCMPSA | 65<br>-<br>23<br>>50 ** |
| Reducing Agents | DTT<br>Cysteine | -<br>- |

FIG. 6A

P1- and P2-substituted Peptide Substrates

| # | Sequence | Cleaved (%) | MOLAR RATIO P89: PEPTIDE/COMPETITION (%) | | | |
|---|---|---|---|---|---|---|
| | | | 1:4 | 1:2 | 1:1 | 1:0.5 |
| P89 | Δ T R P I I T T A * G P S D M Y V H | 100 (50) | <5 | 0 | 0 | 0 |
| E9 | T R P I I T T A * G P S D M Y V | 100 (50) | 0 | 0 | 0 | 0 |
| F2 | T R P I I T T L * G P S D M Y V | 49 (27) | | | | |
| F6 | T R P I I T T V * G P S D M Y V | 28 (7) | | | | |
| F8 | T R P I I T T P  G P S D M Y V | 0 | — | <5 | 0 | 0 |
| F10 | T R P I I T T M * G P S D M Y V | 100 (91) | | | | |
| F12 | T R P I I T T T * G P S D M Y V | 98 (49) | | | | |
| G5 | T R P I I T T N * G P S D M Y V | 16 (10) | 75 | — | <5 | 0 |
| G7 | T R P I I T T Q * G P S D M Y V | 39 (20) | — | — | 0 | 0 |
| G9 | T R P I I T T E  G P S D M Y V | 0 | — | — | 0 | 0 |
| G11 | T R P I I T T D  G P S D M Y V | 0 | — | 0 | 0 | 1 |
| H2 | T R P I I T T Y * G P S D M Y V | 100 (51) | | | | |
| H4 | T R P I I T T K * G P S D M Y V | 19 (8) | | | | |
| H6 | T R P I I T T R * G P S D M Y V | 55 (24) | | | | |
| H12 | T R P I I T T F * G P S D M Y V | 92 (40) | | | | |
| P146 | Δ T R P I I T T Y * G P S D M Y V H | 100 (66) | | | | |
| F | Δ I V T R P I I T T Y * G P S D M Y V H | 100 (63) | | | | |

FIG.6B

| # | Sequence | Cleaved (%) | MOLAR RATIO P89: PEPTIDE/COMPETITION (%) | | | |
|---|---|---|---|---|---|---|
| | P1- AND P2-SUBSTITUTED PEPTIDE SUBSTRATES | | 1:4 | 1:2 | 1:1 | 1:0.5 |
| A1  | T R P I I T G A G P S D M Y V | 0 | — | <5 | 0 | 0 |
| A3  | T R P I I T V A G P S D M Y V | 0 | — | <5 | 0 | 0 |
| A5  | T R P I I T A A G P S D M Y V | 0 | — | <5 | 0 | 0 |
| A7  | T R P I I T L A G P S D M Y V | 0 | — | <10 | 0 | 0 |
| A9  | T R P I I T H A G P S D M Y V | 0 | — | — | 0 | 0 |
| A11 | T R P I I T P A * G P S D M Y V | 5(>1) | — | <10 | <5 | 0 |
| B4  | T R P I I T S A * G P S D M Y V | 9(4) | 55 | 30 | 15 | 0 |
| B6  | T R P I I T H A * G P S D M Y V | <1(0) | — | 0 | 0 | 0 |
| B8  | T R P I I T N A * G P S D M Y V | 30(15) | — | <15 | 5 | 0 |
| B10 | T R P I I T Q A * G P S D M Y V | 12(4) | — | — | 5 | 0 |
| B12 | T R P I I T E A G P S D M Y V | 0 | — | 0 | 0 | 0 |
| C1  | T R P I I T D A G P S D M Y V | 0 | — | 0 | 0 | 0 |
| C3  | T R P I I T K A G P S D M Y V | 5(3) | — | >5 | 5 | 0 |
| C5  | T R P I I T R A * G P S D M Y V | 7(>1) | — | — | 0 | 0 |
| C7  | T R P I I T Y A * G P S D M Y V | <1(0) | <10 | <5 | 0 | 0 |
| D2  | T R P I I T F A G P S D M Y V | 0 | — | 0 | 0 | 0 |

FIG.7A

P1'-, P2'- and P3'-substituted Peptide Substrates

| # | Sequence | Cleaved (%) | \multicolumn{4}{c}{MOLAR RATIO P89: PEPTIDE/COMPETITION (%)} | | | |
|---|---|---|---|---|---|---|
| | | | 1:4 | 1:2 | 1:1 | 1:0.5 |
| P89 | T R P I I T T A * G P S D M Y V H | 100(50) | <5 | 0 | 0 | 0 |
| E9 | T R P I I T T A * G P S D M Y V | 100(50) | 0 | 0 | 0 | 0 |
| D4 | T R P I I T T A * (F) P S D M Y V | 0 | — | 0 | 0 | 0 |
| D6 | T R P I I T T A * (D) P S D M Y V | 0 | — | — | <5 | 0 |
| D8 | T R P I I T T A * (K) P S D M Y V | 0 | — | — | <5 | 0 |
| D10 | T R P I I T T A * (T) P S D M Y V | 0 | — | 15 | <10 | 0 |
| D12 | T R P I I T T A * G (F) S D M Y V | 32(10) | | | | |
| E1 | T R P I I T T A * G (D) S D M Y V | 26(12) | | | | |
| E3 | T R P I I T T A * G (K) S D M Y V | 35(21) | — | 40 | 20 | — |
| E5 | T R P I I T T A * G (T) S D M Y V | 37(19) | | | | |
| C9 | T R P I I T T A * G P (D) D M Y V | 38(8) | | | | |
| E7 | T R P I I T T A * G P (T) D M Y V | 94(41) | | | | |
| H8 | T R P I I T T A * G P (K) D M Y V | 92(43) | | | | |

FIG. 7B

| # | Sequence | Cleaved (%) | MOLAR RATIO P89: PEPTIDE/COMPETITION (%) | | | |
|---|---|---|---|---|---|---|
| | | | 1:4 | 1:2 | 1:1 | 1:0.5 |
| | D-amino acid- and CARBA-Substituted Peptide Substrates | | | | | |
| P2dT | T R P I I T (t) A G P S D M Y V H | 0 | — | 0 | 0 | 0 |
| C11 | T R P I I T (a) A G P S D M Y V H | 0 | 15 | <5 | 0 | 0 |
| H10 | T R P I I T T (a) G P S D M Y V H | 0 | — | 0 | 0 | 0 |
| P2'dP | T R P I I T T A G (p) S D M Y V H | 0 | <5 | 0 | 0 | 0 |
| Capro | T R P I I T T (ε-cap) P S D M Y V H | 0 | 15 | <5 | 0 | 0 |
| STAT | T R P I I T T (stat) P S D M Y V H | 0 | — | <15 | <10 | — |
| | Reference Peptides (Cleavage Products) | | | | | |
| 89/12 ● | T R P I I T T A | 0 | 10 | <5 | 0 | 0 |
| 89/13 ○ |                 G P S D M Y V H | 0 | — | 0 | 0 | 0 |
| UP | T R P I I T T A | 0 | >5 | <5 | 0 | 0 |
| DOWN |                 G P S D M Y V H | 0 | — | 0 | 0 | — |
| P46 ● |       I T T A | 0 | — | 0 | 0 | 0 |
| P47 ○ |                 G P S | 0 | — | 0 | 0 | 0 |

FIG.8A

2A-Substrates of Polio (PV1) and Various Rhinoserotypes

| # | | Sequence | Cleaved (%) | MOLAR RATIO P89: PEPTIDE/COMPETITION (%) | | | |
|---|---|---|---|---|---|---|---|
| | | | | 1:4 | 1:2 | 1:1 | 1:0.5 |
| P89 | △ | T R P I I T T A * G P S D M Y V H | 100(50) | <5 | 0 | 0 | 0 |
| RV14 | | (R K G D I)(K S Y)(G)(L G P R)(Y)(G G) | 0 | | | | |
| P73 | △ | (S T K D L T T)(Y) * (G F G H Q N K A) | 5(2) | — | 0 | 0 | 0 |
| P76 | o | (G F G H Q N K A) | 0 | 0 | 0 | 0 | 0 |
| P75 | △ | (M Q K L L D T)(Y)(G I N L P L V)(T) | 0 | — | — | 0 | 0 |
| P74 | o | (G I N L P L V)(T) | 0 | >15 | 10 | <10 | |
| RV85 | | (E)(R A S L)T T A * G P S D M Y V H | 48(18) | | | | |
| RV39 | | (P R E N L)T T A * G P S D M Y V H | 11(5) | | | | |
| RV1A | | (R R N T)I T T A * G P S D M Y V H | 10(4) | | | | |
| RV1B | | (P R A S M K)(T)(V) * G P S D M Y V H | 10(4) | — | 0 | 0 | 0 |
| RV49 | | (S R A)I I T T A * G P S D M Y V H | 53(23) | | | | |
| RV89 | | D V F T (V)(T)(N V) * G P S (S) M (F) V H | 0 | | | | |
| RV9 | | (N V R A V K N V) * G P S D M Y V H | 0 | | | | |

FIG. 8B

| # | Sequence | Cleaved (%) | 1:4 | 1:2 | 1:1 | 1:0.5 |
|---|---|---|---|---|---|---|
| | | | MOLAR RATIO P89: PEPTIDE/COMPETITION (%) | | | |
| | Truncated and Deleted Peptide Substrates | | | | | |
| P39 | Δ   I T T A   G P S | 0 | — | — | 0 | 0 |
| P145 | Δ  I I T T A   G P S D M | 0 | 70 | — | 0 | 0 |
| WTC9 | Δ   I T T A   G P S D M | 0 | — | 0 | 0 | 0 |
| WTD8 | Δ   I T T A   G P S D | 0 | 55 | <5 | 0 | 0 |
| WT9 | Δ  P I I T T A   G P S | 0 | 0 | 0 | 0 | 0 |
| WT10 | Δ  P I I T T A   G P S D | 0 | 0 | 0 | — | — |
| WTN9 | Δ  T R P I I T T A * G | 9 | 0 | 0 | — | — |
| AB1 | T R P I I T   G P S D M Y V H | 0 | — | — | <5 | 0 |
| AB2 | T R P I I T T   P S D M Y V H | 0 | 30 | 15 | <5 | 0 |
| ST2 | R P I I T T   P S D M Y V H | 0 | — | 5 | <5 | 0 |
| | C-terminal Peptide of HRV2 2A | | | | | |
| P77 | G G D N H V A F I D L R H F H C A E E Q | 0 | — | 0 | 0 | — |

FIG. 9

| NAME | SEQUENCE | RELATIVE CLEAVAGE EFFICIENCY $(V_{max}/K_m)rel$ |
|---|---|---|
| | P1*P1' | |
| P89 | TRPIITTA*GPSDMYVH | 1.00 |
| E9 | TRPIITTA*GPSDMYV | 0.96 |
| F6 | TRPIITTv*GPSDMYV | 0.03 |
| F2 | TRPIITTl*GPSDMYV | 0.38 |
| F8 | TRPIITTp*GPSDMYV | NO CLEAVAGE |
| H12 | TRPIITTf*GPSDMYV | 0.79 |
| F10 | TRPIITTm*GPSDMYV | 5.10 |
| F12 | TRPIITTt*GPSDMYV | 0.68 |
| H2 | TRPIITTy*GPSDMYV | 1.38 |
| G5 | TRPIITTn*GPSDMYV | 0.10 |
| G7 | TRPIITTq*GPSDMYV | 0.11 |
| G11 | TRPIITTd*GPSDMYV | NO CLEAVAGE |
| G9 | TRPIITTe*GPSDMYV | NO CLEAVAGE |
| H6 | TRPIITTr*GPSDMYV | 0.56 |
| H4 | TRPIITTk*GPSDMYV | 0.12 |
| A5 | TRPIITaA*GPSDMYV | NO CLEAVAGE |
| A3 | TRPIITvA*GPSDMYV | NO CLEAVAGE |
| A7 | TRPIITlA*GPSDMYV | NO CLEAVAGE |
| A9 | TRPIITiA*GPSDMYV | NO CLEAVAGE |
| A11 | TRPIITpA*GPSDMYV | 0.06 |
| D2 | TRPIITfA*GPSDMYV | NO CLEAVAGE |

FIG. 10

| NAME | SEQUENCE | RELATIVE CLEAVAGE EFFICIENCY $(V_{max}/K_m)rel$ |
|---|---|---|
| A1 | TRPIITgA*GPSDMYV | NO CLEAVAGE |
| B4 | TRPIITsA*GPSDMYV | 0.15 |
| C7 | TRPIITyA*GPSDMYV | NO CLEAVAGE |
| B8 | TRPIITnA*GPSDMYV | 0.10 |
| B10 | TRPIITqA*GPSDMYV | 0.03 |
| C1 | TRPIITdA*GPSDMYV | NO CLEAVAGE |
| B12 | TRPIITeA*GPSDMYV | NO CLEAVAGE |
| C3 | TRPIITkA*GPSDMYV | 0.05 |
| C5 | TRPIITrA*GPSDMYV | 0.16 |
| B6 | TRPIIThA*GPSDMYV | 0.04 |
| D4 | TRPIITTA*fPSDMYV | NO CLEAVAGE |
| D10 | TRPIITTA*tPSDMYV | NO CLEAVAGE |
| D6 | TRPIITTA*dPSDMYV | NO CLEAVAGE |
| D8 | TRPIITTA*kPSDMYV | NO CLEAVAGE |
| D12 | TRPIITTA*GfSDMYV | 0.28 |
| E5 | TRPIITTA*GtSDMYV | 0.37 |
| E1 | TRPIITTA*GdSDMYV | 0.22 |
| E3 | TRPIITTA*GkSDMYV | 0.43 |
| E7 | TRPIITTA*GPtDMYV | 0.74 |
| C9 | TRPIITTA*GPdDMYV | 0.23 |
| H8 | TRPIITTA*GPkDMYV | 0.76 |

FIG. 11

| NAME | SEQUENCE | RELATIVE CLEAVAGE EFFICIENCY $(V_{max}/K_m)rel$ |
|---|---|---|
| | P1*P1' | |
| P89 | TRPITTA*GPSDMYVH | 1.00 |
| RV49 | sRaITTA*GPSDMYVH | 0.30 |
| RV85 | eRaslTTA*GPSDMYVH | 0.31 |
| RV1A | rRntITTA*GPSDMYVH | 0.01 |
| RV39 | pRenlTTA*GPSDMYVH | 0.04 |
| P73 | slkdlTTy*GgfhqnkA | 0.02 |
| RV14 | rkgdlksy*GlgprYgg | NO CLEAVAGE |
| RV1B | pRasmkTV*GPSDMYVH | 0.03 |
| RV9 | nvravknv*GPSDMYVH | NO CLEAVAGE |
| RV89 | dvftvTnv*GPSsMfVH | NO CLEAVAGE |

SEQUENCE LISTING ( 1 ) GENERAL INFORMATION:

( i i i ) NUMBER OF SEQUENCES: 91

( 2 ) INFORMATION FOR SEQ ID NO:1:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

CATGGGCCCG AGTGACATGT ATGTTCATGT AG      32

( 2 ) INFORMATION FOR SEQ ID NO:2:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GTAACCTACA TGAACATACA TGTCACTCGG GCC      33

( 2 ) INFORMATION FOR SEQ ID NO:3:

( i ) SEQUENCE CHARACTERISTICS:
        ( A ) LENGTH: 16 amino acids
        ( B ) TYPE: amino acid
        ( D ) TOPOLOGY: linear ( x i ) SEQUENCE DESCRIPTION: SEQ ID NO:3:

Thr Arg Pro Ile Ile Thr Thr Ala Gly Pro Ser Asp Met Tyr Val His
1              5                          10                 15

( 2 ) INFORMATION FOR SEQ ID NO:4:

( i ) SEQUENCE CHARACTERISTICS:
        ( A ) LENGTH: 7 amino acids
        ( B ) TYPE: amino acid
        ( D ) TOPOLOGY: linear ( x i ) SEQUENCE DESCRIPTION: SEQ ID NO:4:

Ile Thr Thr Ala Gly Pro Ser
1              5

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( D ) TOPOLOGY: linear ( x i ) SEQUENCE DESCRIPTION: SEQ ID NO:5:

```
    Ile Ile Thr Thr Ala Gly Pro Ser Asp Met
    1               5                  10
```

( 2 ) INFORMATION FOR SEQ ID NO:6:

( i ) SEQUENCE CHARACTERISTICS:
    ( A ) LENGTH: 8 amino acids
    ( B ) TYPE: amino acid
    ( D ) TOPOLOGY: linear ( x i ) SEQUENCE DESCRIPTION: SEQ ID NO:6:

```
    Ile Thr Thr Ala Gly Pro Ser Asp
    1               5
```

( 2 ) INFORMATION FOR SEQ ID NO:7:

( i ) SEQUENCE CHARACTERISTICS:
    ( A ) LENGTH: 14 amino acids
    ( B ) TYPE: amino acid
    ( D ) TOPOLOGY: linear ( x i ) SEQUENCE DESCRIPTION: SEQ ID NO:7:

```
    Thr Arg Pro Ile Ile Thr Thr Pro Ser Asp Met Tyr Val His
    1               5                  10
```

( 2 ) INFORMATION FOR SEQ ID NO:8:

( i ) SEQUENCE CHARACTERISTICS:
    ( A ) LENGTH: 15 amino acids
    ( B ) TYPE: amino acid
    ( D ) TOPOLOGY: linear ( x i ) SEQUENCE DESCRIPTION: SEQ ID NO:8:

```
    Thr Arg Pro Ile Ile Thr Thr Asn Gly Pro Ser Asp Met Tyr Val
    1               5                  10                  15
```

( 2 ) INFORMATION FOR SEQ ID NO:9:

( i ) SEQUENCE CHARACTERISTICS:
    ( A ) LENGTH: 14 amino acids
    ( B ) TYPE: amino acid
    ( D ) TOPOLOGY: linear ( x i ) SEQUENCE DESCRIPTION: SEQ ID NO:9:

```
    Thr Arg Ile Ile Thr Ser Ala Gly Pro Ser Asp Met Tyr Val
    1               5                  10
```

( 2 ) INFORMATION FOR SEQ ID NO:10:

( i ) SEQUENCE CHARACTERISTICS:
    ( A ) LENGTH: 15 amino acids
    ( B ) TYPE: amino acid
    ( D ) TOPOLOGY: linear ( x i ) SEQUENCE DESCRIPTION: SEQ ID NO:10:

```
    Thr Arg Pro Ile Ile Thr Asn Ala Gly Pro Ser Asp Met Tyr Val
    1               5                  10                  15
```

( 2 ) INFORMATION FOR SEQ ID NO:11:

( i ) SEQUENCE CHARACTERISTICS:
    ( A ) LENGTH: 15 amino acids
    ( B ) TYPE: amino acid
    ( D ) TOPOLOGY: linear ( x i ) SEQUENCE DESCRIPTION: SEQ ID NO:11:

```
    Met Gly Pro Ser Asp Met Tyr Val Xaa Val Xaa Xaa Leu Ile Xaa
    1               5                  10                  15
```

( 2 ) INFORMATION FOR SEQ ID NO:12:

( i ) SEQUENCE CHARACTERISTICS:
    ( A ) LENGTH: 15 amino acids
    ( B ) TYPE: amino acid
    ( D ) TOPOLOGY: linear ( x i ) SEQUENCE DESCRIPTION: SEQ ID NO:12:

```
Met Gly Pro Ser Asp Met Tyr Val His Val Gly Asn Leu Ile Tyr
1               5                   10                  15
```

( 2 ) INFORMATION FOR SEQ ID NO:13:

( i ) SEQUENCE CHARACTERISTICS:
    ( A ) LENGTH: 11 amino acids
    ( B ) TYPE: amino acid
    ( D ) TOPOLOGY: linear ( x i ) SEQUENCE DESCRIPTION: SEQ ID NO:13:

```
Thr Thr Ala Gly Pro Ser Asp Met Tyr Val His
1               5                   10
```

( 2 ) INFORMATION FOR SEQ ID NO:14:

( i ) SEQUENCE CHARACTERISTICS:
    ( A ) LENGTH: 12 amino acids
    ( B ) TYPE: amino acid
    ( D ) TOPOLOGY: linear ( x i ) SEQUENCE DESCRIPTION: SEQ ID NO:14:

```
Ile Thr Thr Ala Gly Pro Ser Asp Met Tyr Val His
1               5                   10
```

( 2 ) INFORMATION FOR SEQ ID NO:15:

( i ) SEQUENCE CHARACTERISTICS:
    ( A ) LENGTH: 13 amino acids
    ( B ) TYPE: amino acid
    ( D ) TOPOLOGY: linear ( x i ) SEQUENCE DESCRIPTION: SEQ ID NO:15:

```
Ile Ile Thr Thr Ala Gly Pro Ser Asp Met Tyr Val His
1               5                   10
```

( 2 ) INFORMATION FOR SEQ ID NO:16:

( i ) SEQUENCE CHARACTERISTICS:
    ( A ) LENGTH: 14 amino acids
    ( B ) TYPE: amino acid
    ( D ) TOPOLOGY: linear ( x i ) SEQUENCE DESCRIPTION: SEQ ID NO:16:

```
Pro Ile Ile Thr Thr Ala Gly Pro Ser Asp Met Tyr Val His
1               5                   10
```

( 2 ) INFORMATION FOR SEQ ID NO:17:

( i ) SEQUENCE CHARACTERISTICS:
    ( A ) LENGTH: 15 amino acids
    ( B ) TYPE: amino acid
    ( D ) TOPOLOGY: linear ( x i ) SEQUENCE DESCRIPTION: SEQ ID NO:17:

```
Arg Pro Ile Ile Thr Thr Ala Gly Pro Ser Asp Met Tyr Val His
1               5                   10                  15
```

( 2 ) INFORMATION FOR SEQ ID NO:18:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO:18:

Thr Arg Pro Ile Ile Thr Thr Ala Gly Pro Ser Asp Met Tyr Val
    1               5                   10                  15

( 2 ) INFORMATION FOR SEQ ID NO:19:

( i ) SEQUENCE CHARACTERISTICS:
        ( A ) LENGTH: 14 amino acids
        ( B ) TYPE: amino acid
        ( D ) TOPOLOGY: linear ( x i ) SEQUENCE DESCRIPTION: SEQ ID NO:19:

Thr Arg Pro Ile Ile Thr Thr Ala Gly Pro Ser Asp Met Tyr
    1               5                   10

( 2 ) INFORMATION FOR SEQ ID NO:20:

( i ) SEQUENCE CHARACTERISTICS:
        ( A ) LENGTH: 13 amino acids
        ( B ) TYPE: amino acid
        ( D ) TOPOLOGY: linear ( x i ) SEQUENCE DESCRIPTION: SEQ ID NO:20:

Thr Arg Pro Ile Ile Thr Thr Ala Gly Pro Ser Asp Met
    1               5                   10

( 2 ) INFORMATION FOR SEQ ID NO:21:

( i ) SEQUENCE CHARACTERISTICS:
        ( A ) LENGTH: 12 amino acids
        ( B ) TYPE: amino acid
        ( D ) TOPOLOGY: linear ( x i ) SEQUENCE DESCRIPTION: SEQ ID NO:21:

Thr Arg Pro Ile Ile Thr Thr Ala Gly Pro Ser Asp
    1               5                   10

( 2 ) INFORMATION FOR SEQ ID NO:22:

( i ) SEQUENCE CHARACTERISTICS:
        ( A ) LENGTH: 10 amino acids
        ( B ) TYPE: amino acid
        ( D ) TOPOLOGY: linear ( x i ) SEQUENCE DESCRIPTION: SEQ ID NO:22:

Thr Arg Pro Ile Ile Thr Thr Ala Gly Pro
    1               5                   10

( 2 ) INFORMATION FOR SEQ ID NO:23:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:23:

Thr Arg Pro Ile Ile Thr Thr Ala Gly
    1               5

( 2 ) INFORMATION FOR SEQ ID NO:24:

( i ) SEQUENCE CHARACTERISTICS:
    ( A ) LENGTH: 13 amino acids
    ( B ) TYPE: amino acid
    ( D ) TOPOLOGY: linear ( x i ) SEQUENCE DESCRIPTION: SEQ ID NO:24:

Pro Ile Ile Thr Thr Ala Gly Pro Ser Asp Met Tyr Val
1               5                   10

( 2 ) INFORMATION FOR SEQ ID NO:25:

( i ) SEQUENCE CHARACTERISTICS:
    ( A ) LENGTH: 11 amino acids
    ( B ) TYPE: amino acid
    ( D ) TOPOLOGY: linear ( x i ) SEQUENCE DESCRIPTION: SEQ ID NO:25:

Pro Ile Ile Thr Thr Ala Gly Pro Ser Asp Met
1               5                   10

( 2 ) INFORMATION FOR SEQ ID NO:26:

( i ) SEQUENCE CHARACTERISTICS:
    ( A ) LENGTH: 12 amino acids
    ( B ) TYPE: amino acid
    ( D ) TOPOLOGY: linear ( x i ) SEQUENCE DESCRIPTION: SEQ ID NO:26:

Pro Ile Ile Thr Thr Ala Gly Pro Ser Asp Met Tyr
1               5                   10

( 2 ) INFORMATION FOR SEQ ID NO:27:

( i ) SEQUENCE CHARACTERISTICS:
    ( A ) LENGTH: 10 amino acids
    ( B ) TYPE: amino acid
    ( D ) TOPOLOGY: linear ( x i ) SEQUENCE DESCRIPTION: SEQ ID NO:27:

Pro Ile Ile Thr Thr Ala Gly Pro Ser Asp
1               5                   10

( 2 ) INFORMATION FOR SEQ ID NO:28:

( i ) SEQUENCE CHARACTERISTICS:
    ( A ) LENGTH: 9 amino acids
    ( B ) TYPE: amino acid
    ( D ) TOPOLOGY: linear ( x i ) SEQUENCE DESCRIPTION: SEQ ID NO:28:

Pro Ile Ile Thr Thr Ala Gly Pro Ser
1               5

( 2 ) INFORMATION FOR SEQ ID NO:29:

( i ) SEQUENCE CHARACTERISTICS:
    ( A ) LENGTH: 10 amino acids
    ( B ) TYPE: amino acid
    ( D ) TOPOLOGY: linear ( x i ) SEQUENCE DESCRIPTION: SEQ ID NO:29:

Ile Ile Thr Thr Ala Gly Pro Ser Asp Met
1               5                   10

( 2 ) INFORMATION FOR SEQ ID NO:30:

( i ) SEQUENCE CHARACTERISTICS:
    ( A ) LENGTH: 15 amino acids (B) TYPE: amino acid
(D) TOPOLOGY: linear (x i) SEQUENCE DESCRIPTION: SEQ ID NO:30:

Thr Arg Pro Ile Ile Thr Thr Leu Gly Pro Ser Asp Met Tyr Val
1               5                   10                  15

(2) INFORMATION FOR SEQ ID NO:31:

(i) SEQUENCE CHARACTERISTICS:
    (A) LENGTH: 15 amino acids
    (B) TYPE: amino acid
    (D) TOPOLOGY: linear (x i) SEQUENCE DESCRIPTION: SEQ ID NO:31:

Thr Arg Pro Ile Ile Thr Thr Val Gly Pro Ser Asp Met Tyr Val
1               5                   10                  15

(2) INFORMATION FOR SEQ ID NO:32:

(i) SEQUENCE CHARACTERISTICS:
    (A) LENGTH: 15 amino acids
    (B) TYPE: amino acid
    (D) TOPOLOGY: linear (x i) SEQUENCE DESCRIPTION: SEQ ID NO:32:

Thr Arg Pro Ile Ile Thr Thr Pro Gly Pro Ser Asp Met Tyr Val
1               5                   10                  15

(2) INFORMATION FOR SEQ ID NO:33:

(i) SEQUENCE CHARACTERISTICS:
    (A) LENGTH: 15 amino acids
    (B) TYPE: amino acid
    (D) TOPOLOGY: linear (x i) SEQUENCE DESCRIPTION: SEQ ID NO:33:

Thr Arg Pro Ile Ile Thr Thr Met Gly Pro Ser Asp Met Tyr Val
1               5                   10                  15

(2) INFORMATION FOR SEQ ID NO:34:

(i) SEQUENCE CHARACTERISTICS:
    (A) LENGTH: 15 amino acids
    (B) TYPE: amino acid
    (D) TOPOLOGY: linear (x i) SEQUENCE DESCRIPTION: SEQ ID NO:34:

Thr Arg Pro Ile Ile Thr Thr Thr Gly Pro Ser Asp Met Tyr Val
1               5                   10                  15

(2) INFORMATION FOR SEQ ID NO:35:

(i) SEQUENCE CHARACTERISTICS:
    (A) LENGTH: 15 amino acids
    (B) TYPE: amino acid
    (D) TOPOLOGY: linear (x i) SEQUENCE DESCRIPTION: SEQ ID NO:35:

Thr Arg Pro Ile Ile Thr Thr Gln Gly Pro Ser Asp Met Tyr Val
1               5                   10                  15

(2) INFORMATION FOR SEQ ID NO:36:

(i) SEQUENCE CHARACTERISTICS:
    (A) LENGTH: 15 amino acids
    (B) TYPE: amino acid
    (D) TOPOLOGY: linear (x i) SEQUENCE DESCRIPTION: SEQ ID NO:36:

Thr Arg Pro Ile Ile Thr Thr Glu Gly Pro Ser Asp Met Tyr Val
1               5                   10                  15

(2) INFORMATION FOR SEQ ID NO:37:

(i) SEQUENCE CHARACTERISTICS:
        (A) LENGTH: 15 amino acids
        (B) TYPE: amino acid
        (D) TOPOLOGY: linear (x i) SEQUENCE DESCRIPTION: SEQ ID NO:37:

Thr Arg Pro Ile Ile Thr Thr Asp Gly Pro Ser Asp Met Tyr Val
1               5                   10                  15

(2) INFORMATION FOR SEQ ID NO:38:

(i) SEQUENCE CHARACTERISTICS:
        (A) LENGTH: 15 amino acids
        (B) TYPE: amino acid
        (D) TOPOLOGY: linear (x i) SEQUENCE DESCRIPTION: SEQ ID NO:38:

Thr Arg Pro Ile Ile Thr Thr Tyr Gly Pro Ser Asp Met Tyr Val
1               5                   10                  15

(2) INFORMATION FOR SEQ ID NO:39:

(i) SEQUENCE CHARACTERISTICS:
        (A) LENGTH: 15 amino acids
        (B) TYPE: amino acid
        (D) TOPOLOGY: linear (x i) SEQUENCE DESCRIPTION: SEQ ID NO:39:

Thr Arg Pro Ile Ile Thr Thr Lys Gly Pro Ser Asp Met Tyr Val
1               5                   10                  15

(2) INFORMATION FOR SEQ ID NO:40:

(i) SEQUENCE CHARACTERISTICS:
        (A) LENGTH: 15 amino acids
        (B) TYPE: amino acid
        (D) TOPOLOGY: linear (x i) SEQUENCE DESCRIPTION: SEQ ID NO:40:

Thr Arg Pro Ile Ile Thr Thr Arg Gly Pro Ser Asp Met Tyr Val
1               5                   10                  15

(2) INFORMATION FOR SEQ ID NO:41:

(i) SEQUENCE CHARACTERISTICS:
        (A) LENGTH: 15 amino acids
        (B) TYPE: amino acid
        (D) TOPOLOGY: linear (x i) SEQUENCE DESCRIPTION: SEQ ID NO:41:

Thr Arg Pro Ile Ile Thr Thr Phe Gly Pro Ser Asp Met Tyr Val
1               5                   10                  15

(2) INFORMATION FOR SEQ ID NO:42:

(i) SEQUENCE CHARACTERISTICS:
        (A) LENGTH: 16 amino acids
        (B) TYPE: amino acid
        (D) TOPOLOGY: linear (x i) SEQUENCE DESCRIPTION: SEQ ID NO:42:

Thr Arg Pro Ile Ile Thr Thr Tyr Gly Pro Ser Asp Met Tyr Val His
1               5                   10                  15

(2) INFORMATION FOR SEQ ID NO:43:

(i) SEQUENCE CHARACTERISTICS:
        (A) LENGTH: 18 amino acids
        (B) TYPE: amino acid
        (D) TOPOLOGY: linear (xi) SEQUENCE DESCRIPTION: SEQ ID NO:43:

Ile Val Thr Arg Pro Ile Ile Thr Thr Tyr Gly Pro Ser Asp Met Tyr
1               5                   10                  15

Val His (2) INFORMATION FOR SEQ ID NO:44:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:44:

Thr Arg Pro Ile Ile Thr Gly Ala Gly Pro Ser Asp Met Tyr Val
1               5                   10                  15

(2) INFORMATION FOR SEQ ID NO:45:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:45:

Thr Arg Pro Ile Ile Thr Val Ala Gly Pro Ser Asp Met Tyr Val
1               5                   10                  15

(2) INFORMATION FOR SEQ ID NO:46:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:46:

Thr Arg Pro Ile Ile Thr Ala Ala Gly Pro Ser Asp Met Tyr Val
1               5                   10                  15

(2) INFORMATION FOR SEQ ID NO:47:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:47:

Thr Arg Pro Ile Ile Thr Leu Ala Gly Pro Ser Asp Met Tyr Val
1               5                   10                  15

(2) INFORMATION FOR SEQ ID NO:48:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:48:

Thr Arg Pro Ile Ile Thr Ile Ala Gly Pro Ser Asp Met Tyr Val
1               5                   10                  15

( 2 ) INFORMATION FOR SEQ ID NO:49:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO:49:

Thr Arg Pro Ile Ile Thr Pro Ala Gly Pro Ser Asp Met Tyr Val
1               5                   10                  15

( 2 ) INFORMATION FOR SEQ ID NO:50:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO:50:

Thr Arg Pro Ile Ile Thr Ser Ala Gly Pro Ser Asp Met Tyr Val
1               5                   10                  15

( 2 ) INFORMATION FOR SEQ ID NO:51:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO:51:

Thr Arg Pro Ile Ile Thr His Ala Gly Pro Ser Asp Met Tyr Val
1               5                   10                  15

( 2 ) INFORMATION FOR SEQ ID NO:52:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO:52:

Thr Arg Pro Ile Ile Thr Gln Ala Gly Pro Ser Asp Met Tyr Val
1               5                   10                  15

( 2 ) INFORMATION FOR SEQ ID NO:53:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO:53:

Thr Arg Pro Ile Ile Thr Glu Ala Gly Pro Ser Asp Met Tyr Val
1               5                   10                  15

( 2 ) INFORMATION FOR SEQ ID NO:54:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO:54:

Thr Arg Pro Ile Ile Thr Asp Ala Gly Pro Ser Asp Met Tyr Val ( 2 ) INFORMATION FOR SEQ ID NO:55:

( i ) SEQUENCE CHARACTERISTICS:
    ( A ) LENGTH: 15 amino acids
    ( B ) TYPE: amino acid
    ( D ) TOPOLOGY: linear ( x i ) SEQUENCE DESCRIPTION: SEQ ID NO:55:

```
Thr Arg Pro Ile Ile Thr Lys Ala Gly Pro Ser Asp Met Tyr Val
1               5                   10                  15
```

( 2 ) INFORMATION FOR SEQ ID NO:56:

( i ) SEQUENCE CHARACTERISTICS:
    ( A ) LENGTH: 15 amino acids
    ( B ) TYPE: amino acid
    ( D ) TOPOLOGY: linear ( x i ) SEQUENCE DESCRIPTION: SEQ ID NO:56:

```
Thr Arg Pro Ile Ile Thr Arg Ala Gly Pro Ser Asp Met Tyr Val
1               5                   10                  15
```

( 2 ) INFORMATION FOR SEQ ID NO:57:

( i ) SEQUENCE CHARACTERISTICS:
    ( A ) LENGTH: 15 amino acids
    ( B ) TYPE: amino acid
    ( D ) TOPOLOGY: linear ( x i ) SEQUENCE DESCRIPTION: SEQ ID NO:57:

```
Thr Arg Pro Ile Ile Thr Tyr Ala Gly Pro Ser Asp Met Tyr Val
1               5                   10                  15
```

( 2 ) INFORMATION FOR SEQ ID NO:58:

( i ) SEQUENCE CHARACTERISTICS:
    ( A ) LENGTH: 15 amino acids
    ( B ) TYPE: amino acid
    ( D ) TOPOLOGY: linear ( x i ) SEQUENCE DESCRIPTION: SEQ ID NO:58:

```
Thr Arg Pro Ile Ile Thr Phe Ala Gly Pro Ser Asp Met Tyr Val
1               5                   10                  15
```

( 2 ) INFORMATION FOR SEQ ID NO:59:

( i ) SEQUENCE CHARACTERISTICS:
    ( A ) LENGTH: 15 amino acids
    ( B ) TYPE: amino acid
    ( D ) TOPOLOGY: linear ( x i ) SEQUENCE DESCRIPTION: SEQ ID NO:59:

```
Thr Arg Pro Ile Ile Thr Thr Ala Phe Pro Ser Asp Met Tyr Val
1               5                   10                  15
```

( 2 ) INFORMATION FOR SEQ ID NO:60:

( i ) SEQUENCE CHARACTERISTICS:
    ( A ) LENGTH: 15 amino acids
    ( B ) TYPE: amino acid
    ( D ) TOPOLOGY: linear ( x i ) SEQUENCE DESCRIPTION: SEQ ID NO:60:

```
Thr Arg Pro Ile Ile Thr Thr Ala Asp Pro Ser Asp Met Tyr Val
1               5                   10                  15
```

( 2 ) INFORMATION FOR SEQ ID NO:61:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO:61:

```
Thr Arg Pro Ile Ile Thr Thr Ala Lys Pro Ser Asp Met Tyr Val
1               5                   10                  15
```

( 2 ) INFORMATION FOR SEQ ID NO:62:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO:62:

```
Thr Arg Pro Ile Ile Thr Thr Ala Thr Pro Ser Asp Met Tyr Val
1               5                   10                  15
```

( 2 ) INFORMATION FOR SEQ ID NO:63:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO:63:

```
Thr Arg Pro Ile Ile Thr Thr Ala Gly Phe Ser Asp Met Tyr Val
1               5                   10                  15
```

( 2 ) INFORMATION FOR SEQ ID NO:64:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO:64:

```
Thr Arg Pro Ile Ile Thr Thr Ala Gly Asp Ser Asp Met Tyr Val
1               5                   10                  15
```

( 2 ) INFORMATION FOR SEQ ID NO:65:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO:65:

```
Thr Arg Pro Ile Ile Thr Thr Ala Gly Lys Ser Asp Met Tyr Val
1               5                   10                  15
```

( 2 ) INFORMATION FOR SEQ ID NO:66:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO:66:

```
Thr Arg Pro Ile Ile Thr Thr Ala Gly Thr Ser Asp Met Tyr Val
1               5                   10                  15
```

( 2 ) INFORMATION FOR SEQ ID NO:67:

( i ) SEQUENCE CHARACTERISTICS:
    ( A ) LENGTH: 15 amino acids
    ( B ) TYPE: amino acid
    ( D ) TOPOLOGY: linear ( x i ) SEQUENCE DESCRIPTION: SEQ ID NO:67:

```
Thr Arg Pro Ile Ile Thr Thr Ala Gly Pro Asp Asp Met Tyr Val
1               5                   10                  15
```

( 2 ) INFORMATION FOR SEQ ID NO:68:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO:68:

```
Thr Arg Pro Ile Ile Thr Thr Ala Gly Pro Thr Asp Met Tyr Val
1               5                   10                  15
```

( 2 ) INFORMATION FOR SEQ ID NO:69:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO:69:

```
Thr Arg Pro Ile Ile Thr Thr Ala Gly Pro Lys Asp Met Tyr Val
1               5                   10                  15
```

( 2 ) INFORMATION FOR SEQ ID NO:70:

( i ) SEQUENCE CHARACTERISTICS:
        ( A ) LENGTH: 8 amino acids
        ( B ) TYPE: amino acid
        ( D ) TOPOLOGY: linear ( x i ) SEQUENCE DESCRIPTION: SEQ ID NO:70:

```
Thr Arg Pro Ile Ile Thr Thr Ala
1               5
```

( 2 ) INFORMATION FOR SEQ ID NO:71:

( i ) SEQUENCE CHARACTERISTICS:
        ( A ) LENGTH: 8 amino acids
        ( B ) TYPE: amino acid
        ( D ) TOPOLOGY: linear ( x i ) SEQUENCE DESCRIPTION: SEQ ID NO:71:

```
Gly Pro Ser Asp Met Tyr Val His
1               5
```

( 2 ) INFORMATION FOR SEQ ID NO:72:

( i ) SEQUENCE CHARACTERISTICS:
        ( A ) LENGTH: 7 amino acids
        ( B ) TYPE: amino acid
        ( D ) TOPOLOGY: linear ( x i ) SEQUENCE DESCRIPTION: SEQ ID NO:72:

```
Gly Pro Ser Asp Met Tyr Val
1               5
```

( 2 ) INFORMATION FOR SEQ ID NO:73:

( i ) SEQUENCE CHARACTERISTICS:

(A) LENGTH: 4 amino acids
            (B) TYPE: amino acid
            (D) TOPOLOGY: linear (xi) SEQUENCE DESCRIPTION: SEQ ID NO:73:

Ile  Thr  Thr  Ala
    1

(2) INFORMATION FOR SEQ ID NO:74:

(i) SEQUENCE CHARACTERISTICS:
            (A) LENGTH: 16 amino acids
            (B) TYPE: amino acid
            (D) TOPOLOGY: linear (xi) SEQUENCE DESCRIPTION: SEQ ID NO:74:

Arg  Lys  Gly  Asp  Ile  Lys  Ser  Tyr  Gly  Leu  Gly  Pro  Arg  Tyr  Gly  Gly
    1                 5                    10                        15

(2) INFORMATION FOR SEQ ID NO:75:

(i) SEQUENCE CHARACTERISTICS:
            (A) LENGTH: 16 amino acids
            (B) TYPE: amino acid
            (D) TOPOLOGY: linear (xi) SEQUENCE DESCRIPTION: SEQ ID NO:75:

Ser  Thr  Lys  Asp  Leu  Thr  Thr  Tyr  Gly  Phe  Gly  His  Gln  Asn  Lys  Ala
    1                 5                    10                        15

(2) INFORMATION FOR SEQ ID NO:76:

(i) SEQUENCE CHARACTERISTICS:
            (A) LENGTH: 8 amino acids
            (B) TYPE: amino acid
            (D) TOPOLOGY: linear (xi) SEQUENCE DESCRIPTION: SEQ ID NO:76:

Gly  Phe  Gly  His  Gln  Asn  Lys  Ala
    1                 5

(2) INFORMATION FOR SEQ ID NO:77:

(i) SEQUENCE CHARACTERISTICS:
            (A) LENGTH: 16 amino acids
            (B) TYPE: amino acid
            (D) TOPOLOGY: linear (xi) SEQUENCE DESCRIPTION: SEQ ID NO:77:

Met  Gln  Lys  Leu  Leu  Asp  Thr  Tyr  Gly  Ile  Asn  Leu  Pro  Leu  Val  Thr
    1                 5                    10                        15

(2) INFORMATION FOR SEQ ID NO:78:

(i) SEQUENCE CHARACTERISTICS:
            (A) LENGTH: 8 amino acids
            (B) TYPE: amino acid
            (D) TOPOLOGY: linear (xi) SEQUENCE DESCRIPTION: SEQ ID NO:78:

Gly  Ile  Asn  Leu  Pro  Leu  Val  Thr
    1                 5

(2) INFORMATION FOR SEQ ID NO:79:

(i) SEQUENCE CHARACTERISTICS:
            (A) LENGTH: 16 amino acids
            (B) TYPE: amino acid (D) TOPOLOGY: linear (xi) SEQUENCE DESCRIPTION: SEQ ID NO:79:

Glu Arg Ala Ser Leu Thr Thr Ala Gly Pro Ser Asp Met Tyr Val His
1               5                   10                  15

(2) INFORMATION FOR SEQ ID NO:80:

(i) SEQUENCE CHARACTERISTICS:
  (A) LENGTH: 16 amino acids
  (B) TYPE: amino acid
  (D) TOPOLOGY: linear (xi) SEQUENCE DESCRIPTION: SEQ ID NO:80:

Pro Arg Glu Asn Leu Thr Thr Ala Gly Pro Ser Asp Met Tyr Val His
1               5                   10                  15

(2) INFORMATION FOR SEQ ID NO:81:

(i) SEQUENCE CHARACTERISTICS:
  (A) LENGTH: 16 amino acids
  (B) TYPE: amino acid
  (D) TOPOLOGY: linear (xi) SEQUENCE DESCRIPTION: SEQ ID NO:81:

Arg Arg Asn Thr Ile Thr Thr Ala Gly Pro Ser Asp Met Tyr Val His
1               5                   10                  15

(2) INFORMATION FOR SEQ ID NO:82:

(i) SEQUENCE CHARACTERISTICS:
  (A) LENGTH: 16 amino acids
  (B) TYPE: amino acid
  (D) TOPOLOGY: linear (xi) SEQUENCE DESCRIPTION: SEQ ID NO:82:

Pro Arg Ala Ser Met Lys Thr Val Gly Pro Ser Asp Met Tyr Val His
1               5                   10                  15

(2) INFORMATION FOR SEQ ID NO:83:

(i) SEQUENCE CHARACTERISTICS:
  (A) LENGTH: 16 amino acids
  (B) TYPE: amino acid
  (D) TOPOLOGY: linear (xi) SEQUENCE DESCRIPTION: SEQ ID NO:83:

Ser Arg Ala Ile Ile Thr Thr Ala Gly Pro Ser Asp Met Tyr Val His
1               5                   10                  15

(2) INFORMATION FOR SEQ ID NO:84:

(i) SEQUENCE CHARACTERISTICS:
  (A) LENGTH: 16 amino acids
  (B) TYPE: amino acid
  (D) TOPOLOGY: linear (xi) SEQUENCE DESCRIPTION: SEQ ID NO:84:

Asp Val Phe Thr Val Thr Asn Val Gly Pro Ser Ser Met Phe Val His
1               5                   10                  15

(2) INFORMATION FOR SEQ ID NO:85:

(i) SEQUENCE CHARACTERISTICS:
  (A) LENGTH: 16 amino acids
  (B) TYPE: amino acid
  (D) TOPOLOGY: linear ( x i ) SEQUENCE DESCRIPTION: SEQ ID NO:85:

Asn Val Arg Ala Val Lys Asn Val Gly Pro Ser Asp Met Tyr Val His
1               5                   10                  15

( 2 ) INFORMATION FOR SEQ ID NO:86:

( i ) SEQUENCE CHARACTERISTICS:
( A ) LENGTH: 9 amino acids
( B ) TYPE: amino acid
( D ) TOPOLOGY: linear ( x i ) SEQUENCE DESCRIPTION: SEQ ID NO:86:

Ile Thr Thr Ala Gly Pro Ser Asp Met
1               5

( 2 ) INFORMATION FOR SEQ ID NO:87:

( i ) SEQUENCE CHARACTERISTICS:
( A ) LENGTH: 14 amino acids
( B ) TYPE: amino acid
( D ) TOPOLOGY: linear ( x i ) SEQUENCE DESCRIPTION: SEQ ID NO:87:

Thr Arg Pro Ile Ile Thr Gly Pro Ser Asp Met Tyr Val His
1               5                   10

( 2 ) INFORMATION FOR SEQ ID NO:88:

( i ) SEQUENCE CHARACTERISTICS:
( A ) LENGTH: 13 amino acids
( B ) TYPE: amino acid
( D ) TOPOLOGY: linear ( x i ) SEQUENCE DESCRIPTION: SEQ ID NO:88:

Arg Pro Ile Ile Thr Thr Pro Ser Asp Met Tyr Val His
1               5                   10

( 2 ) INFORMATION FOR SEQ ID NO:89:

( i ) SEQUENCE CHARACTERISTICS:
( A ) LENGTH: 20 amino acids
( B ) TYPE: amino acid
( D ) TOPOLOGY: linear ( x i ) SEQUENCE DESCRIPTION: SEQ ID NO:89:

Gly Gly Asp Asn His Val Ala Phe Ile Asp Leu Arg His Phe His Cys
1               5                   10                  15

Ala Glu Glu Gln
            20

( 2 ) INFORMATION FOR SEQ ID NO:90:

( i ) SEQUENCE CHARACTERISTICS:
( A ) LENGTH: 16 amino acids
( B ) TYPE: amino acid
( D ) TOPOLOGY: linear ( x i ) SEQUENCE DESCRIPTION: SEQ ID NO:90:

Ser Leu Lys Asp Leu Thr Thr Tyr Gly Gly Phe His Gln Asn Lys Ala
1               5                   10                  15

( 2 ) INFORMATION FOR SEQ ID NO:91:

( i ) SEQUENCE CHARACTERISTICS:
( A ) LENGTH: 16 amino acids
( B ) TYPE: amino acid
( D ) TOPOLOGY: linear ( x i ) SEQUENCE DESCRIPTION: SEQ ID NO:91:

```
Arg  Lys  Gly  Asp  Leu  Lys  Ser  Tyr  Gly  Leu  Gly  Pro  Arg  Tyr  Gly  Gly
1                   5                        10                        15
```

EXPRESSION OF MATURE PROTEINASE 2A, THE PARTIAL PURIFICATION THEREOF AND PREPARATION OF SUBSTRATES HAVING AN INHIBITORY EFFECT

This application is a continuation, of application Ser. No. 07/971,619, filed November 6, 1992, now abandoned.

BACKGROUND OF THE INVENTION

1. Field of the Invention

The invention relates to the preparation of mature HRV2 proteinase 2A, the partial purification thereof and the preparation of substrates having an inhibitory effect.

2. Background Information

Numerous animal and plant viruses require an input of vitally-coded proteinases during their replication cycle. The Picorna viruses, a family of significant viruses pathogenic to humans and animals, are for example totally dependent on proteolytic processing. The proteolytic enzymes involved in the replication are highly substrate-specific and generally recognise a cleavage region—i.e. a structurally determined recognition feature—and, to a lesser extent, an accurately defined amino acid pair such as is generally used as a recognition sequence. A general survey on this subject is provided by Kräusslich, H. G. and Wimmer, E. (*Ann. Rev. Biochem.* 57:701–751 (1988)) and Kay, J. and Dunn, B. M. (*Biochim. Biophys. Acta* 1048:1–18 (1990)).

In view of their substrate specificity and their catalytic mechanism the viral proteinases constitute a good therapeutic point of attack (Johnston, M. I. et al., *Trends Pharmacol. Sci.* 10:305–307 (1989)). By preparing the three-dimensional structure of the proteinases of Rous Sarcoma Virus (Leis, J. et al., ASM-News 56:77–81 1990)) and of HIV I (Navia, M. A. et al., *Nature* 337:615–620 (1989); Miller, M. et al., *Science* 246:1149–1152 (1989)) it is possible to carry out computer-aided molecular designing of highly specific inhibitors (Meek, T. D. et al., *Nature* 343:90–92 (1990)). Specific proteinase inhibitors could therefore be new antiviral substances directed, for example, against viruses for which it is not possible to develop a vaccine for purely technical reasons; e.g., in the ease of rhinoviruses, there are at present well over 115 serotypes which do not crossreact with one another, 90 of which have already been classified as definite serotypes (Cooney, M. K. et al., *Infect. Immun.* 37:642–647 (1982)).

Proteolytic processing of the polyprotein (Jacobson, M. F. and Baltimore, D., *Proc. Natl. Acad. Sci.* 83:5392 (1968)) by vitally coded proteinases is preferably found in (+)-strain RNA viruses (Hellen, C. U. T. et al., *Biochemistry* 28:9881–9890 (1989)) and in retroviruses (Skalka, A. M., *Cell* 56:911–913 (1989)). By means of molecular biology studies, sequence comparisons and X-my structural analysis it has been found that the proteinases coded by viruses can be put into two categories of proteolytic enzymes, namely the pepsin-like aspartate proteinases (Meek, T. D. et al., *Proc. Natl. Acad. Sci.* 86:1841–1845 (1989)) and the cysteine-proteinases with trypsin-like protein chain folding (Bazan, J. F. and Fletterick, R. J., *Proc. Natl. Acad. Sci.* 85:7872–7876 (1988)). It is not always only virally coded proteinases which are involved in the proteolytic processing of viral polyprotein; for example, cellular proteinases participate in the maturation cleavage of the polyprotein of Yellow Fever Virus which belongs to Flaviviridae (Ruiz-Linares, A. et al., *J. Virol.* 63:4199–4209 (1989)).

The substrate specificity of the viral enzymes has been analysed more closely by detailed studies such as point mutation analysis, cleaving of peptide substrates in vitro and amino acid sequencing of the native cleavage products. It was found that, as already mentioned hereinbefore, it is less the cleavage site itself than some positions upstream or downstream which play a significant part in the recognition of cleavage sites. However, this sequence heterogeneity of the cleavage signals or their immediate environment results in a kind of "hierarchy" of the cleavage events in the polyprotein (Kräusslich, H. G. et al., *Proc. Natl. Acad. Sci.* 86:807–811 (1989); Pichuantes, S. et al., PROTEINS: Structure, Function and Genetics 6:324–337 (1989); Darke, P. L. et al., *J. Biol. Chem.* 264:2307–2312 (1989); Nicklin, M. J. H. et al., *J. Virol.* 62:4586–4593 (1988); Libby, R. T. et al., *Biochemistry* 27:6262–6268 (1988); Sommergruber, W. et al., *Virology* 169:68–77 (1989)). The variation of the individual cleavage regions in the polyprotein thus permits a precisely determined sequence from kinetically "favorable" to kinetically "unfavorable" cleavages which then make it possible to carry out differential proteolysis of the individual cleavage products. Consequently, the viral proteinases have a kind of regulatory potential during the viral replication cycle. The principle of recognition of a specific secondary structure in the cleavage site area is not limited to Picorna viruses but would appear to be a general principle of viral proteinases. Thus, for example, these properties are also found in the adenovirus system (Webster, A. et al., *J. Gen. Virol.* 70:3225–3234 (1989); Webster, A. et al., *J. Gen. Virol.* 70:3215–3223 (1989) and in plant viral systems as well (Carrington, J. C. and Dougherty, W. G., *Proc. Natl. Acad. Sci.* 85:3391–3395 (1988); Dougherty, W. G. et al., *EMBO J.* 7:1281–1288 (1988)).

Hardly any other viral system is so dependent, for the regulation of the course of infection, on a controlled, limited proteolysis as the Picorna viridae system. This family of viruses can be subdivided into four different genera: entero-, rhino-, aphto- and cardioviruses. Rhinoviruses, like all other viruses of this family, are single-stranded (+)RNA viruses (Cooper, P. D. et al., *Intervirology* 10:165–180 (1978); MacNaughton, M. R., *Current Top. Microbiol. Immunol.* 97:1–26 (1982)). They are widespread, attack the upper respiratory tract in humans and cause acute infections which lead to catarrh, coughs, sore throat etc. and are generally referred to as colds (Stott, E. J. and Killington, R. A., *Ann. Rev. Microbiol.* 26:503–524 (1972)). Rhinovirus infections are among the commonest illnesses in man. The disease usually runs its course without any problems but, as the result of temporary weakening of the organism, there may be secondary infections caused by other viruses or bacteria which may in certain circumstances result in serious illness. Of the total of about 115 known different serotypes of human rhinoviruses, hitherto five serotypes (HRV 1B, 2, 9, 14 and 89) have been cloned and completely sequenced: German Patent Application P 35 05 148.5; Skern; T. et al., *Nucleic Acids Res.* 13:2111–2126 (1985); Düchler, M. et al., *Proc. Natl. Acad. Sci. USA* 84:2605–2609 (1987); Stanway, G. et al., *Nucleic Acids Res.* 12:7859–7877 (1984); Callahan, P. L. et al., *Proc. Natl. Acad. Sci. USA* 82:732–736 (1985); Hughes, R. et al., *J. Gen. Virol.* 69:49–58 (1988); Lecki, G. W., Ph.D. Thesis, University of Reading (1988)).

The genomie single-strand (+)RNA of the rhinoviruses is modified shortly after the infection by cleaving of the oligopeptide VPg bound to the 5' end and is subsequently used as mRNA for synthesizing a polyprotein which includes the entire continuous reading frame of the nucleic acid sequence (Butterworth, B. E., *Virology* 56:439–453

(1973); McLean, C. and Rueckert, R. R., *J. Virol.* 11:341–344 (1973); McLean, C. et al., *J. Virol.* 19:903–914 (1976); Agol, V. I., *Prog. Med. Virol.* 26:119–157 (1980); Putnak, J. R. and Phillips, B. A., *Microbiol. Rev.* 45:287–315 (1981)). The mature viral proteins are formed solely by proteolytic cleaving from this polyprotein whilst—in the case of entero- and rhinoviruses at least—the proteinases which are effective are themselves part of this polyprotein. Processing is carried out in 3 stages (Palmenberg, A., *J. Cell. Blochem.* 33:191–198 (1987); Kräusslich, H. G. and Wimmer, E., loc. cit. (1988)):

1.) primary cleavage: separation of the capsid precursor from the growing polypeptide chain;
2.) secondary cleavage: processing of structural and non-structural precursor proteins and
3.) mature cleavage of the capsid.

The first step therefore serves to cleave the precursor of the coat proteins and (in the case of entero- and rhinoviruses) is carried out autocatalytically by the proteinase 2A (cis-activity). The sequence of proteinase 2A (hereinafter referred to as 2A) is immediately after the section which codes for the coat proteins. Thus, in view of its location in the polyprotein, 2A is the first detectable enzymatic function of the virus. The separation of the coat protein region from the section responsible for replication occurs during the actual translation of the polyprotein "in statu nascendi". Experiments in vitro have shown that, in the poliovirus, this primary cleaving may be carried out at the P1-P2 region intermolecularly, i.e. "in trans" by the mature proteinase 2A (Kräusslich, H. G. and Wimmer, E., loc. cit. (1988)). The cleavage signal which is thus recognized by the proteinase 2A has been, on the one hand, determined by direct amino acid sequence analysis of the N-terminus of 2A and/or the C-terminus of VP1 or, on the other hand, derived by comparison of the primary structure on the basis of homology studies. In polio (Pallansch, M. A. et al., *J. Virol.* 49:873–880 (1984)), BEV and HRV14 (Callahan, P. L. et al., loc. cit. (1985)) it is a Tyr/Gly amino acid pair, in HRV2 (Kowalski, H. et al., *J. Gen. Virol.* 86:3197–3200 (1987); Sommergruber, W. et al., *Virology* 169:68–77 (1989)) it is an Ala/Gly amino acid pair, in HRV1B (Hughes, P. J. et al., *J. Gen. Virol.* 69:49–58 (1988)) and HRV89 (Düchler, M. et al., loc. cit. (1987)) it is a Val/Gly pair and in Cox B1 (Iizuka, N. et al., *Virology* 156:64–73 (1987)), Cox B3 (Lindberg, A. M. et al., *Virology* 156:50–63 (1987)) and Cox B4 (Jenkins, O. et al., *J. Gen. Virol.* 68:1835–1848 (1987)) it is a Thr/Gly amino acid pair. This step is essential for the further progress of the viral infection (compartmentralization of replication and virus assembly). In cardioviruses and aphtoviruses, by contrast with the polioviruses, this cleaving is catalysed by proteinase 3C (Kräusslich, H. -G. and Wimmer, E., loc. cit. (1988)). As regards the poliovirus system it is known that probably all the enzymes participating in this maturation cleavage are virally coded (Toyoda, H. et al., *Cell* 45:761–770 (1986)). In the poliovirus there are three types of cleavage signals; specific amino acid pairs Q-G which are recognized by the viral proteinase 3C (hereinafter referred to as 3C), the above-mentioned Y-G pair which serves as the 2A recognition signal and the N-S cleavage signal used in the mature cleavage of the capsid.

As has already been explained, the course of the infection in the case of picornaviruses is critically dependent on the viral enzymes. Since these very enzymes are particularly well conserved and are very similar in their properties in various rhinoviruses, they constitute an ideal target for chemotherapeutic intervention, e.g. the viral enzyme 2A. The chemotherapeutic point of attack is the inhibition of enzymatic activity by specific inhibitors. If the first proteolytic activity, the 2A activity, is inhibited, this prevents any further maturation of the viral system. Surprisingly, the 2A region of HRV2 has a marked homology not only with other rhinoviruses but also with viruses from other groups of the picornaviridae. An inhibitor against HRV2 2A might therefore be capable of being used on other picornaviruses.

The general importance of inhibiting virally coded proteinases has been moved back into the spotlight of possible antiviral therapeutic approaches not least by studies with the proteinase of human immunodeficiency virus 1 (HIV I). By deletion and point mutations in the proteinase region of this kind of retrovirus, it has been possible to recognise the essential role of the proteinase in the maturation of this type of virus (Katoh, I. et al., *Virol.* 145:280–292 (1985); Kohl, N. E. et al., *Proc. Natl. Acad. Sci.* USA 85:4686–4690 (1988); Crowford, S. and Goff, S. P., *J. Virol.* 53:899–907 (1985)). It has also been shown, by X-ray structural analysis and molecular biological studies, that the proteinase of HIV I belongs to the Asp-type, can process itself on the precursor protein (in recombinant prokaryotic systems as well), is capable of cleaving "in trans" specific peptides and occurs as an active proteinase in a homodimeric form (Navia, M. A. et al., loc. cit. (1989); Meek, T. D. et al., loc. cit. (1989); Katoh, I. et al., loc. cit. (1985)). In view of the fact that the proteinase of HIV I occurs as a dimer in its active form, Wlodawer and colleagues also proposed the development of specific dimerization inhibitors (Wlodawer, A. et al., *Science* 245:616–621 (1989)). The development of highly specific competitive inhibitors against the proteinase of HIV I on the basis of modified peptide substrates was described only recently by Tomasselli and colleagues (Tomasselli, A. G. et al., *Biochem.* 29:264–269 (1990)). It had been known for even longer that a fungicidal antibiotic, cerulenin, has an antiretroviral activity against Rous Sarcoma Virus and Murine Leukemia Virus (Goldfine, H. et al., *Biochem. Biophys. Acad.* 512:229–240 (1978); Katoh, I. et al., *Virus Res.* 5:265–276 (1986)). In the case of HIV I, it was possible to make a connection between the inhibitory effect of cerulenin and the inhibition in the proteolytic processing of the polyprotein of HIV I (Pal, R. et al., *Proc. Natl. Acad. Sci.* 85:9283–9286 (1988)). Starting from this fact, Blumenstein and colleagues were able to develop specific inhibitors against proteinase HIV I on the basis of synthetic non-peptide inhibitors. In other words, they were able to trace the inhibitory effect of cerulenin to the interaction of the electrophilic epoxide group with nucleophilic regions of the proteinase. Moreover, as a result of the development of synthetic derivatives, the original toxicity of cerulenin has been reduced (Blumenstein, J. J. et al., *Biochem. Biophys. Res. Commun.* 163:980–987 (1989)).

Also in the picornaviral system, all kinds of organic or inorganic compounds as well as peptide derivatives and proteins are now known which have an inhibitory effect on the proteolytie processing of these viruses. The effect of these substances is based on the direct interaction with the proteinases (Kettner, C. A. et al., U.S. Pat. No. : 4,652,552 (1987); Korant, B. D. et al., *J. Cell. Blochem.* 32:91–95 (1986) and/or on the indirect route of interaction with substrates of these proteinases (Geist, F. C. et al., *Antimicrob. Agents Chemother.* 31:622–624 (1987); Perrin, D. D. and Stünzl, H., *Viral Chemotherapy* 1:288–189 (1984)). The problem with the majority of these substances is the relatively high concentration required for inhibition and the toxicity of these compounds, which is considerable with some of them. The already successful use of modified peptides and peptidomimeties as therapeutic agents in nonviral areas (Fauchere, J. L., *Advanc. Drug Res.* 15:29–69 (1986)) and inhibitor designing starting from known structures (DesJarlais, R. L. et al., "Viral Proteinases as Targets for Chemotherapy", in *Curr. Commun. Mol. Biol.*, Cold Spring Harbor Laboratory Press, 203–210 (1989)) and the increase in molecular biological and physical data on picornaviral proteases has increased the understanding of the structure and function of these viral enzymes and thus permits a stepwise rational designing—starting from modified peptide substrates—to achieve highly specific and non-toxic peptidomimetics.

The first evidence of a second virally coded proteinase, 2A, came from antibodies developed against polio P3C which clearly suppressed all the cleaving carried out at Q-G but did not suppress cleaving between Y-G (Hanecak, R. et al., *Proc. Natl. Acad. Sci. USA* 79:3973–3977 (1982)). This observation lead to the conclusion that the proteolytic processing at Y-G sites requires its own proteinase. The seat of this second proteolytic activity could clearly be ascribed to 2A in poliovirus. It was interesting to discover 2A carries out alternative cleaving in the proteinase-polymerase region (3CD), which also occurs at a Y-G site and yields inactive enzymes 3C' and 3D'. This cleaving possibly serves to regulate the quantities of the enzymes 3C and 3D (Lee, C. K. and Wirrueruer, E., *Virol.* 166:1435–1441 (1988)). Since the synthesis of host protein is very rapidly stopped during infection with poliovirus in HeLa cells, but the translation of the poliovirus RNA is able to proceed unhindered, it was assumed that one or more regulating factors of the translation were changed during the infection. In fact, earlier findings show that the eukaryotic initiation factor 4F is changed by the proteolytic cleaving of the p220 component during the poliovirus infection in HeLa cells (Etchison, D. et al., *J. Virol.* 51:832–837 (1984); Etchison, D. et at., *J. Biol. Chem.* 257:14806–14810 (1982), Etchison, D. and Etchison, J. R., *J. Virol.* 61:2702–2710 (1987)). It was subsequently demonstrated that 2A is indirectly responsible for this modification of p220 in infected cells (Kräusslich, H. G. et al., *J. Virol.* 61:2711–2718 (1987); Lloyd, R. E. et al., *Virol.* 150:299–303 (1986); Lloyd, R. E. et al., *J. Virol.* 61:2450–2488 (1987)). The question of the "trans" activity of the proteinase 2A was first answered in the affirmative in the poliovirus system, by making insertions and deletions in 2A to express an unprocessed P1-P2 region in *E. coli* which was able to be cleaved from poliovirus, which either came from cells infected with poliovirus (Nicklin, M. J. H., et al., *Proc. Natl. Acad. Sci.* USA, 84:4002–4006 (1987)), or was translated "in vitro" (Kräusslich, .-G. et al., *J. Virol.* 61:2711–2718 (1987)) or expressed in *E. coli,* or purified from cells infected with poliovirus (König, and Rosenwirth, B., *J. Virol.* 62:1243–1250 (1988)). Bernstein and colleagues were able to distinguish between a "cis"- and a "trans"-active form of the proteinase 2A using Poliovirus mutants. These routants contain an additional Leu between the 102 and 103 amino acids of 2A. This Leu insertion lead to a poorly replicating but still viable poliovirus. No cleavage of the cellular p220 molecules could be observed in HeLa cells infected with these mutants (Bernstein, H. D., et al., *Mol. Cell. Biol.* 5:2913–2923 (1985); Bernstein, H. D., et al., *J. Virol.* 60:1040–1049 (1986)).

With the aid of recombinant vaceinia vectors which contained the complete P1 region and the gene section for a shortened inactive form of proteinase 2A from polio, it was shown that after coinfection with one of the three serotypes of polio, with HRV14 or with EMCV both in the cases of polio 1, 2 and 3 and also in the case of HRV14, correct intermolecular ("trans") processing occurred at the P½A cutting site. After coinfection with EMCV, there was no processing of the inactive precursor protein of polio (Jewell, J. E., et al., *J. Virol.* 64:1388–1393 (1990)). Moreover, in higher eukaryotic cells it was demonstrated, by means of expression vectors under the control of the LTR region of HIV I and activated by means of the "tat" gene product, that 2A from poliovirus is the inducing agent in the proteolysis of p220 (Sun, X. H. and Baltimore, D., *Proc. Natl. Acad. Sci.* 86:2143–2146 (1989)). Kräusslich and his collaborators also showed that although the presence of an active 2A is absolutely necessary for the proteolytic degradation of p220 during the host cell shutoff, this degradation is not directly carried out by 2A (Kräusslich, H. G. et al., loc. cit. (1987)). It is currently presumed that the proteinase 2A is capable of activating a cellular enzyme which consequently brings about the cleaving of p220. Recent investigations have given rise to speculation that possibly the $Ca^{2+}$-dependent cellular proteinase calpain may be responsible for this "p220-ase" activity. According to this model, the proteinase 2A would convert an inactive calpain into an active form by cleaving it and the active form would then attack the p220. The possible cleaving of the calpain might occur 80 amino acids away from the N-terminus in the sequence Y-G (Wyckoff, E. E. and Ehrenfeld, E., EUROPIC 89, "Sixth Meeting of the European Study Group on the Molecular Biology of Picornaviruses," Bruges, Belgium (1989)).

Possibly, the two proteinases 2A and 3C are directly or indirectly involved in the proteolytic degradation of another 14 cellular proteins during the infection of HeLa cells with poliovirus (Urzainqui, A. and Carrasco, L., *J. Virol.* 63:4729–4735 (1989)).

The most recent data show that poliovirus proteinase 2A inhibits not only the translation of the host cell but also the DNA replication and the RNA polymerase II transcription (Davies, M. V., et al., *J. Biol. Chem.* 266:14714–14720 (1991)).

As a result of these data the various 2A proteinases of the individual entero- and rhinoviruses would have to recognise one or more common targets in the cell. Therefore, the understanding and knowledge of the trans-substrate specificity of 2A is of great importance.

Hitherto, it has only been possible to express the 2A of HRV2 as a fusion protein. As a result of the autocatalytic activity the mature proteinase is cleaved from the precursor molecule after expression. Owing to the poor solubility of the precursor protein and the cleaved proteinase itself, however, this process involves a significant loss of yield, which means that the mature proteinase released is present in a very small concentration (Sommergruber et al., loc. cit. (1989)).

SUMMARY OF THE INVENTION

It is a general object of this invention to provide a DNA molecule comprising a DNA vector and a DNA segment encoding an HRV proteinase 2A or variant thereof.

It is a specific object of this invention to provide a DNA molecule comprising a DNA vector and a DNA segment encoding an HRV proteinase 2A or variant thereof wherein the variant arises from mutation, deletion or insertion and the molecule is capable of expressing HRV proteinase 2A or variant thereof.

It is another object of the invention to provide a cell that that contains the above-described DNA molecule.

It is a further object of the invention to provide a method of purifying an HRV 2A proteinase comprising expressing the proteinase in the above-described cell, and purifying the proteinase.

It is another object of the invention to provide a peptide or chemical derivative thereof derived by N- or C-terminal shortening or by altering the ITTAG motif of the amino acid sequence set forth in SEQ ID NO:3, wherein the peptide or chemical derivative thereof has an inhibitory effect on rhinoviral HRV2 2A protease.

It is a further object of the invention to provide a pharmaceutical composition comprising the above-described peptide in an amount effective to inhibit HRV 2A proteinase in an animal and a pharmaceutically acceptable diluent, carrier, adjuvant, stabilizer, or excipient.

Further objects and advantages of the present invention will be clear from the description that follows.

BRIEF DESCRIPTION OF THE DRAWINGS

FIG. 1A shows the elution profile of the Wild type proteinase 2A, FIG. 1B shows the elution profile of the inactive variant 9B (Cys106:Ser). The NaCl gradient used here (30% to 50%) is also shown. The specific proteolytic activity (% cleaving of P89) of each fraction is indicated by blocked-in circles and by a broken line. The lower part of FIGS. 1A and 1B shows a Western blot analysis of the MONO Q fractions. The position and molecular weight of the marker proteins are shown on the right-hand side of each Western blot. The capital letters indicate the position of the Wild type 2A (FIG. 1A) or the mutant 9B (FIG. 1B). The numbers at the top of the Western blot denote the fraction numbers of the MONO Q column. C is a positive control derived from the known expression system for 2A (pEx2A; Sommergruber et al., loc. cit. (1989)).

FIG. 2. pH-dependency of the proteolytic activity of HRV2 2A (% cleaving of P89 against pH). The closed circles indicate the activity obtained when investigating the enzyme at a pH shown on the x-axis. Open squares denote the activity obtained with pre-incubation of 2A at the pH value given for 20 minutes at ambient temperature with subsequent trans-cleavage assay of the sample at pH 8.0 to 8.5. The arrows and capital letters indicate the buffer system used in this experiment. A: sodium citrate/HCl, B: glycine/NaOH; C: glycine/HCl; D: phthalic acid/NaOH; E: Tris/HCl; F: $CH_3COOH$/NaOH and G: $NaH_2PO_4$/$Na_2HPO_4$.

FIG. 5. $IC_{50}$ values for HRV2 2A in the presence of known proteinase inhibitors and reducing agents. An asterisk (*) indicates that, when PMSF is used, no linear dependency of inhibition could be shown (presumably a problem of solubility). A double asterisk (**) indicates that no exact information as to the concentration can be given owing to the poor solubility of pCMPSA.

FIGS. 6A and 6B. Clearability of the peptide substrates and/or their ability to act as inhibitors. P1- and P2-substituted peptide substrates.

FIGS. 7A and 7B. Cleavability of the peptide substrates and/or their ability to act as inhibitors. P1'- P2'-, P3'-, D-amino acid and CARBA- substituted peptide substrates.

FIGS. 8A and 8B. Cleavability of the peptide substrates and/or their ability to act as inhibitors. Peptide substrates derived from poliovirus type 1 and the alternative cleavage site thereof in 3D (P75) and from rhinovirus 1A, 1B, 9, 14, 39, 49, 85 or 89 as well as shortened and deleted Wild-type peptide substrates. The emboldened letters shown in a frame indicate a substitution, deletion or abbreviation. Small emboldened letters relate to the D-amino acid analogues. ε-cap and stat denote the exchange of the amino acid pair Ala-Gly for ε-aminocaproic acid or statine. An asterisk indicates the cleavage site identified. The abbreviations for each peptide are shown on the left-hand side. An open triangle denotes the peptides which have an acetyl group at their amino terminus and an $NH_2$ group at their carboxy terminus. Open circles relate to the sole presence of an $NH_2$ group at the C-terminus and a closed circle indicates the sole presence of an acetylated N-terminus. The peptide sequences and their clearability are listed in the centre part of the Figure as % cleavage as compared with the Wild-type substrate P89, after 32 minutes' incubation under the conditions described in Example 2. The percentages given in brackets indicated the percentage cleavability of the particular peptide at the moment when 50% cleavage of the Wild-type substrate P89 or E9 has occurred. The right-hand side of the Figures shows the ability of non-cleavable or slightly clearable peptides to act as competitors with P89 (0.11 mM) at the molar ratios specified.

FIG. 9. Representation of the relative cleavage efficiency of substituted synthetic peptides by HRV2 2A (small letters denote exchanged amino acids). Competitive cleavage reactions were carried out as described in the Examples; the efficiency of a cleavage is expressed as $(V_{max}/K_m)_{rel}$ with P89 as the reference peptide. All the peptides are cleaved at the cleavage site indicated by an asterisk.

FIG. 10: Continuation of FIG. 9.

FIG. 11: Relative cleavage efficiency of synthetic peptides derived from various rhino- and poliovirus 2A cleavage sites. A dot shows that the P' region is derived from HRV2; small letters indicate amino acids which differ from those obtained from HRV2; competitive cleavage reactions were carried out as described in the Examples; the cleavage efficiency is expressed with peptide P89 as reference peptide. All the peptides cleaved are cleaved at the site marked by an asterisk.

Figures 1, 1A:
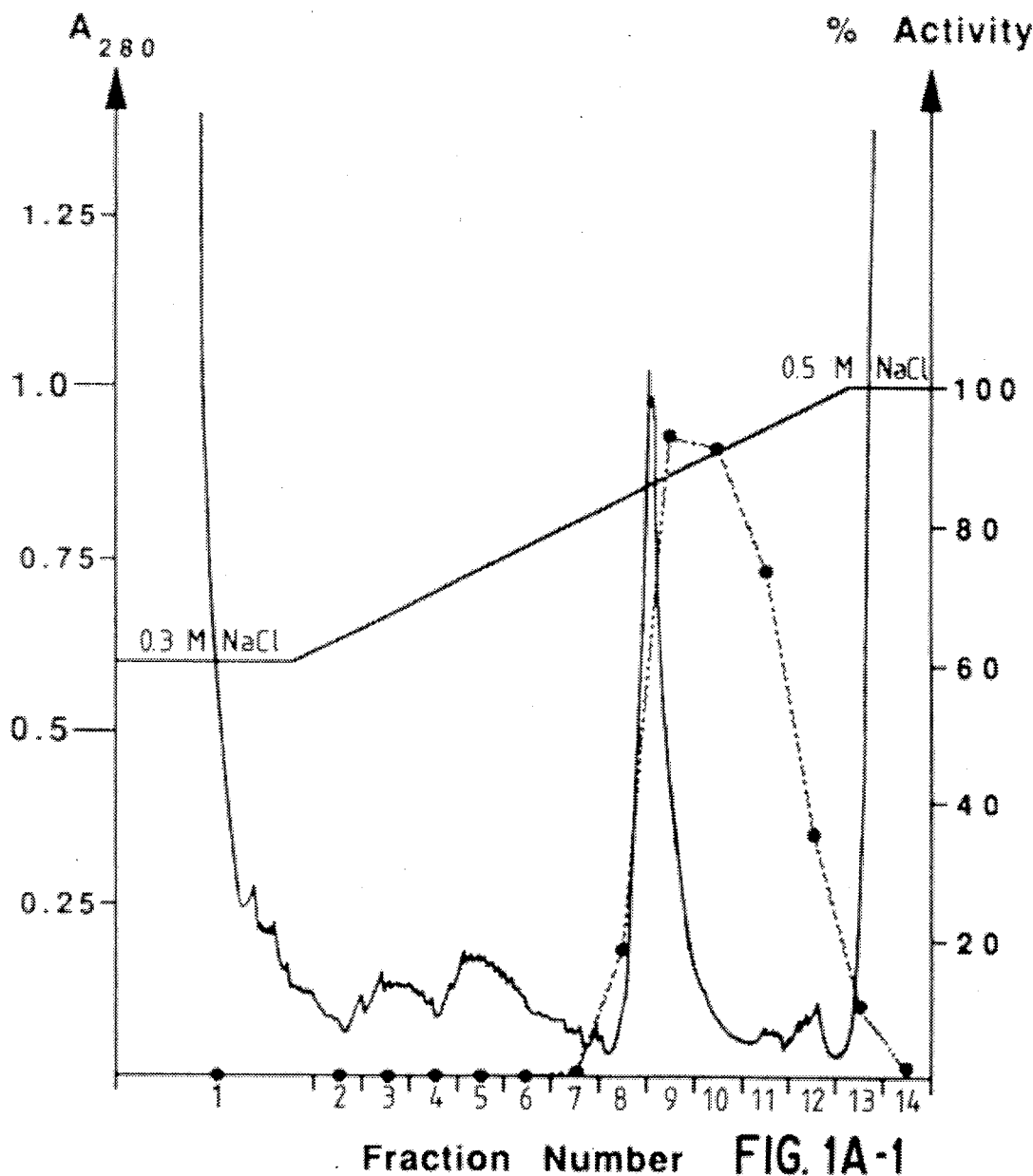
FIGS. 1A-1, 1A-2, 1B-1, and 1B-2 $OD_{280}$-profiles of the MONO Q-fractions of active and inactive HRV2 2A proteinase including Western blot analysis.

| Abbreviations | |
|---|---|
| PSMF: | Phenylmethanesulphonylfluoride |
| TLCK: | Tosyllysylchloromethylketone |
| TPCK: | Tosylphenylalanylchloromethylketone |
| APMSF: | 4-(Amidinophenyl)methanesulphonylfluoride |
| HOBr: | 1-Hydroxybenzotriazolmonohydrate |
| DIPCDI: | N,N'-Diisopropylcarbodiimide |
| Mtr: | 4-Methoxy-2,3,6-trimethylbenzosulphonyl |
| Pmc: | 2,2,5,7,8-Pentamethylchroman-6-sulphonyl |
| tBu: | Tert-butyl- |
| Trt: | Trityl- |
| Boc: | Butyloxycarbonyl |
| Fmoc: | 9-Fluorenylmethoxycarbonyl |
| TFA: | Trifluoroacetic acid |
| IPTG: | Isopropylthiogalactoside |

| Abbreviations | |
|---|---|
| BSA: | Bovine serum albumin |
| DMSO: | Dimethylsulphoxide |
| DTT: | Dithiothreitol |

DETAILED DESCRIPTION OF THE INVENTION

The aim of the present invention is to provide a process for expressing a mature HRV2 2A proteinase, a simple method of partial purification, peptide substrates for clarifying the trans-substrate specificity as well as peptides with an inhibitory effect.

Surprisingly, a process has now been found which enables bacterial expression of the mature proteinase 2A both in a good yield and with a relatively good solubility. For this purpose the DNA coding for the proteinase (Sommergruber et al., loc. cit. (1989)) is cloned into an inducible vector. Example 1 describes, in an advantageous embodiment of the invention, the cloning of the BstEII/HindIII fragment from pEx2A (Sommergruber et al., loc. cit. (1989)), which comprises the majority of the coding region of the 2A proteinase with the exception of the first 11 N-terminal amino acids, as well as the oligonucleotide (SEQ ID NO:1 and SEQ ID NO:2)

```
5-  CATGGGCCCGAGTGACATGTATGTTCATGTAG         -3
3-         CCGGGCTCACTGTACATACAAGTACATCCAATG  -5,
``` which comprises the missing N-terminal 2A amino acids including a start codon, into the expression vector P PROK-1 (CLONTECH Laboratories) linearised with NcoI and HindIII. An analogous procedure is also possible for expressing enzymatically inactive, mature HRV 2A variants. Example 1 describes the cloning of corresponding BstEII/HindIII fragments from pEx2A (Cys106:Ser) and pEx2A (ΔGly/107/108) (Sommergruber et al., loc. cit. (1989)). In order to express the 2A, the vector containing the complete gene, advantageously p pROK-½A-41 or, for an enzymatically inactive variant, p PROK-⅓B or p PROK-1/I1 in E. coli, preferably in E. coli HB 101, is transformed by known methods. Cultivation can then take place in LB medium, for example, at 35° C. (with the addition of the corresponding antibiotic) for 8 hours ($OD_{600}$=1.75) and after dilution (1:10) and further incubation for 2 hours ($OD_{600}$=1,10) induced with IPTG (final concentration: 0.5 mM). After about 13 hours induction ($OD_{600}$=2.2) the cells can be worked up. Surprisingly, under the conditions of growth described, the A maximum amount of the proteinase is present in soluble form (about 15 to 20% of the total amount of 2A).

The cells which can be separated by centrifuging may be broken up by methods known per se, e.g. using ultrasound. The supernatant obtained from the cell extract by centrifuging (Example 2) can be further purified by ion exchange chromatography, preferably on MONO Q material. Surprisingly, this one purification step is sufficient to separate off the interfering proteolytic activity caused by the endogenous E. coli proteinases (Example 3). In an advantageous embodiment, the supernatant purified after centrifugation and ultracentrifugation (buffer: 50 mM Tris-HCl (pH 8.5), 5 mM DTT) is placed on a MONO Q 5/5 column. Elution is carried out with a salt gradient, preferably with a 30% to 50% NaCl gradient (elution buffer A:50 mM Tris-HCl (pH 8.5), 5 mM DTT; elution buffer B: 50 mM Tris-HCl (pH 8.5), 5 mM DTT, 1M NaCl). The fractions containing the 2A may be recognized, for example, by the correct cleaving of the 16-mer peptide P89, which corresponds to the Wild-type cutting site (Example 3, Sommergruber et al., loc. cit. (1989)). The fractions containing an inactive proteinare may be identified by immunological methods known per se (Examples 2 and 3, Sommergruber et al., loc. cit. (1989)). The fractions which contain the proteinase 2A are combined, placed on 8% glycerol, 1 mg/ml acetylated BSA (bovine serum albumin) and can be stored after freezing in liquid nitrogen at −20° C. The enzymatic activity is largely maintained with only a small loss of 5 to 10%.

Using this process it is possible to obtain all the HRV 2A proteinases, preferably the HRV2 2A proteinase and the active and inactive HRV2 2A proteinase variants produced by mutations, deletions and/or insertions, preferably the inactive variants 9B and 1I. The correct N-terminus may be checked, for example, by amino acid sequencing. Since a large part of the protein material produced by the process described is blocked for sequencing, each 2A preparation preferably contains formylated N-terminal methionine.

Thus, the invention includes DNA vectors which contain a sequence coding for an HRV 2A proteinase, as well as the variants which can be produced by mutations, deletions and/or insertions, which code for an enzymatically active or inactive HRV 2A proteinase and are characterised in that they permit expression of the mature protein. The DNA vectors are preferably the plasmids PROK-¼₁ PROK-½ or PROK-1/9B. The invention also relates to host organisms containing the vectors described above, preferably E. coli, and especially E. coli HB 101. The invention also relates to a process for expressing the above-mentioned proteinases, characterized in that a host organism is transformed with a DNA vector mentioned above and the corresponding proteinase is expressed and purified, as well as a process for purifying a proteinase produced by the recombinant method, characterized in that the corresponding proteinase is expressed as described above and purified by anionic ion exchange chromatography, preferably using Mono Q material.

The preparation of an enzymatically active proteinase or a partially purified fraction of an enzymatically active proteinase opens up the possibility of investigating the effect of the proteinase on substrates.

The process of Example 3 can be used to analyze the cleavage kinetics of substrates of the 2A proteinase. The enzyme preparations partially purified by chromatography on MONO Q columns are mixed with a peptide substrate and the products are detected with the aid of reverse phase HPLC and/or identified by the comigration of comparison peptides and/or by amino acid analysis. The peptide substrate may, for example, be the 16-mer peptide "P89" (acetyl-TRPIITTA*GpSDMyVH-NH₂)(SEQ ID NO:3) which contains the Wild-type cutting site of the proteinase 2A and is specifically cleaved at the amino acid pair Ala-Gly (FIG. 1A).

Figures 1, 1A, 2:
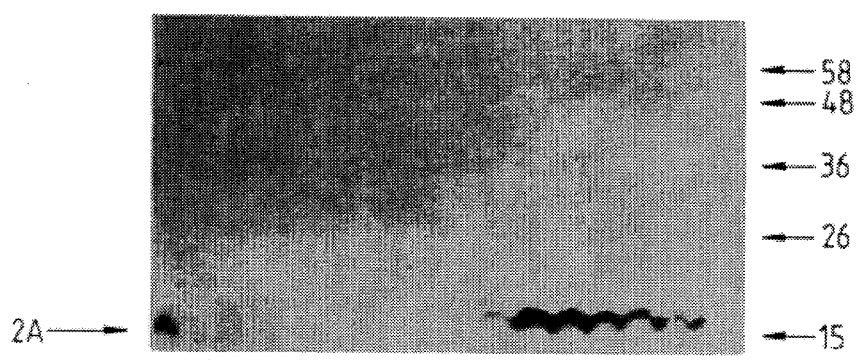

In order to analyse the peptide cleavage (Trans-Cleavage-Assay) 100 μl of a MONO Q fraction containing a 2A proteinase are incubated with the corresponding peptide (5 μl of an aqueous peptide solution with 4 to 2 mg/ml) at 34° C. for 2, 4, 8, 16 and 32 minutes. For competitive or inhibitory experiments the corresponding substance is added in 5 μl volumes. The reactions are stopped using 0.5M HClO₄. After further processing (Example 3) the reaction products can be analyzed as described. The analysis of the pH dependency of the HRV2 2A proteinase carried out in this way in Example 3 is shown in FIG. 2. The Figure shows that the proteinase 2A is not irreversibly destroyed at lower pH levels. The enzyme regains its activity after retitration of pH levels of between 4 to 9 back to pH 8.5. The curve thus shows that kinetically important ionisations are more likely to occur on acidic than on basic amino acid side groups.

Figure 3:
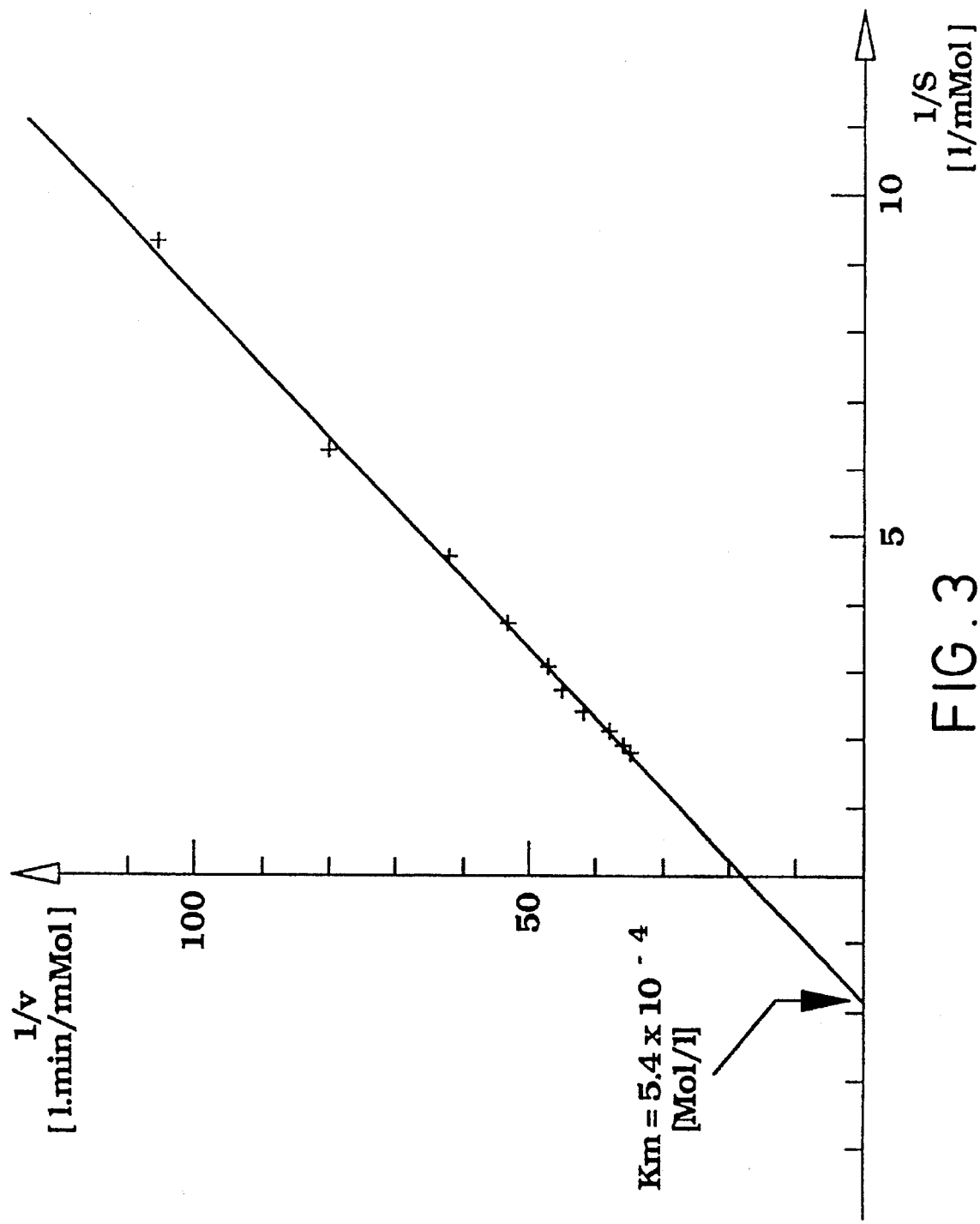
FIG. 3. Lineweaver-Burk diagram for the Km determination of the peptide substrate P89.

Trans-cleavage assays were also carried out to determine the Km-value ($(5.4\pm0.02)\times10^{-4}$ mol/l) with the peptide substrate P89 (Example 5, FIG. 3).

The effect of a series of known inhibitors of serine, cysteine, aspartate and metalloproteinases and also the effect of reducing agents on the activity of 2A as compared with peptide P89 can be investigated by means of trans-cleavage-assays. The trans-cleavage-assays were carried out as described above, except that the various proteinase inhibitors were added before the start of the reaction. The kinetic investigations which were repeated three times with freshly prepared and stabilised 2A preparations show a high degree of reprodueibility. FIG. 5 shows that specific aspartate inhibitors and typical metalloproteinase inhibitors have no effect on the transactivity, with the exception of EDTA and 1,10-phenanthrolene, which demonstrate a certain inhibiting effect at higher concentrations. A similar effect has been described for some trypsin-like proteinases and for calpains, which are admittedly stabilized by $Ca^{2+}$ but are not dependent thereon. (North, in: "Prevention of Unwanted Proteolysis" in *Proteolytic Enzymes* (A Practical Approach), Beynon and Bond, eds., IRL Press, Oxford (1989)). SH-reactive agents such as iodacetamide and N-ethylmaleimide strongly inhibit the proteinase 2A, whereas E-64 (a specific Cys-proteinase inhibitor) has no effect. A peptide aldehyde inhibitor of the Cys-proteinases (antipain) and two peptide aldehyde inhibitors of the Ser proteinases (chymostatin and elastatinal) are highly effective against 2A. The ineffectiveness of Leupeptine (a peptide aldehyde inhibitor of the Cys proteinases) could be put down to its low effective concentration, which is possibly caused by the hydration of the aldehyde group (Beynon and Salvesen, in: *Proteolytic Enzymes* (A Practical Approach), Beynon and Bond, eds., IRL Press, Oxford, 241–249, (1989)). TLCKL, PMSF and TPCK, which are known for their inhibitory effect on cysteine proteinases by non-specific alkylation of sulphhydryl groups of the enzymes (Rich, in: *Proteinase Inhibitors*, Barrett and Salvesen, Amsterdam, Elsevier, 153–178 (1986)), are only effective at higher concentrations. Other Ser-proteinase inhibitors such as APMSF and 3,4-dichloroisocumarin (Beynon and Salvesen, loc. cit. (1989)) show no activity against the HRV2 2A. Reducing agents such as DTT and cysteine have no effect. On the basis of the investigations by Bazan and Fletterick (FEBS Lett. 249:5–7 (1989)) and Sommergruber et al. (loc. cit. (1989)) cysteine (Cys 106) was proposed as an active nucleophilic agent. However, the investigations with polio 2A carried out by Koenig and Rosenwirth (*J. Virol.* 62:1243–1250 (1988)) and Yu and Lloyd (*Virology* 182:615–625 (1991)) as well as the data now available show that the proteinases and in this case HRV2 2A cannot clearly be categorized as cysteine proteinases.

The preparation of substrates of the HRV2 2A protease with an inhibitory effect will now be described, these substrates being charaeterised in that they are derived from the amino acid motif TRPIITTAGPSDMYVH (SEQ ID NO:3) and are obtained by C- or N-terminal shortening and/or the amino acid motif ITTAGPS (SEQ ID NO:4) is altered.

It has been shown that a peptide 16 amino acids long (P89) which covers the region between the C-terminus of VP1 and the aminoterminus of 2A, may be an effective substrate for the proteinase 2A (Sommergruber et al., loc. cit. (1989)). The suitability of shorter peptides as substrates was investigated by trans-cleavage assays (under identical conditions to those described in Example 3) and compared with P89. The results are assembled in FIG. 4. Successive C-terminal deletions within P89 (peptides E9, WT14, WTC13, WTD12, CWT10 and WTN9) have a much reduced influence on clearability than N-terminal deletions (peptides A, B, C, D and E). Reductions in the length of the amino terminal end of P89 beyond the amino acid proline (position P6) result in a reduction in the cleavability by one order of magnitude. This part of the peptide is crucial for effective recognition and cleavability (peptides C and D). By comparison, however, the minimum number of one amino acid (peptide WTN9) on the carboxy-terminal end is sufficient for a cleavage. Consequently, the C-terminal end plays a smaller role in the substrate recognition and/or cleavage. Degradation of both ends of the peptide substrate results in an 11-mer substrate (WTC 11) which can be cleaved efficiently (40%). Further degradation of both ends does not allow any further cleavage. A change in solubility as the reason for differences in clearability has not been observed under the test conditions (Example 8).

Rhinoviral 2A proteinases recognize an Ala or Val at position P 1 and a Gly at position P1', with the exception of the proteinase 2A of HRV14, which cleaves a Tyr-Gly bond, similarly to the serotypes of the poliovirus. Coxsackie virus have a Thr-Gly cleavage sequence at their VP1–2A cutting site. The majority of cleavage signals of the rhino- and enteroviruses have a Thr at position P2 and/or P3 (Kräusslich and Wimmer, 1988, loc. tit. ). Only HRV14 and HRV9 have no Thr at one of these positions (Stanway et al., *Nucl. Acids Res.* 11:5629–5643 (1983); Lecki, G. W., loc. cit. (1988)). Moreover, all the known rhinovirus strains have a proline at position P2' with the exception of HRV 14. The cleavage efficiency can be determined using modified peptide substrates (mutations at positions P2, P1, P 1', P2' and P3' (Example 8)). A 15-mer Wild type substrate (E9, FIGS. 6–9)) may be used as a comparison, for example. Any influence on the charge distribution can be ruled out (Example 8). The cleavage sites occurring can be determined by comigration with corresponding reference peptides.

Surprisingly, it has now been found that the mutation analyses indicated a high tolerance against exchanges at positions P1, P2' and P3', but indicated an absolute dependency on threonine of P2 and glycine of P 1' (FIGS. 6 and 7). HRV2 2A at position P2 tolerates only exchanges of amino acids which are closest to Thr in size and polarity (peptides B4, B8 and B12; FIG. 6). Peptides with positively charged groups in position P2 (peptides C3 and C5) showed a degree of cleavability, although sharply reduced. One possible interpretation of the acceptance of positive charges at this position would be the structural similarity to trypsin-like proteinases (Bazan and Fletterick, loc. cit.) which are known to cleave according to basic amino acids. All other mutations in the peptide substrate result in the peptide no longer being able to be cleaved by 2A (FIG. 6). The position P2 therefore seems to play an essential part (in addition to the ITTA motif and the Arg at position P7). Peptide inhibitors should therefore contain, at position P2, groups which result in a strong interaction between the substrate and the proteinase, e.g. the use of modified amino acids with reactive side chains such as α-amino-isobutyric acid, vinylglycine, homocysteine, homoserine, β-cyanoalanine or S-methylcysteine-sulphoxide. A Tyr-Gly cleavage signal from poliovirus strains and HRV14 (Kitamura et al., *Nature* 291:547–553 (1981); Toyoda et al., *J. Mol. Biol.* 174:561–585 (1984); Stanway et al., loc. cit. (1983)) as well as Thr-Gly signals from the Coxsackie viruses B1, B3 and B4 can be cleaved efficiently (Iizuka et al., *Virology* 156:64–73 (1987); Linberg et al., *Virology* 156:50–63 (1987); Jenkins et al., *J. Gen. Virol.* 68:1835–1848 (1987)). By comparing the percentage clearability of the peptide mutants at a moment when there is 50% cleavage of the Wild type substrates (P89 and E9) it was possible to demonstrate that there is a higher cleavage efficiency in the presence of a Met or Tyr in position P1 (peptides F10, H2, P146 and F) (FIG. 6). These two groups in P1 would appear to create a kinetically more favorable trans-activity for the HRV2 2A.

Measurement of the relative cleavage efficiency ($V_{max}/K_m)_{rel}$ values) according to Pallai et al. (*J. Biol. Chem.* 264:9738–9741 (1989)) confirms the above remarks. FIGS. 9 and 10 show the relative cleavage efficiency for peptides with a single amino acid exchange.

Taken together, these results demonstrate the importance of positions P2 and P1' for the enzyme-substrate interaction and/or for stabilizing the peptide structure.

FIG. 11 demonstrates the cleavage efficiency of HRV2 2A for peptides derived from other rhino- and polioviral 2A cleavage sites.

Furthermore, deletions can be inserted in the Wild type substrate (peptides AB1, AB2 and ST2) to check whether the proteinase 2A also accepts other, less dominant cleavage signals within a peptide, as described for the Cys activity of polio 2A (Hellen et al., in: "Viral Proteinases as Targets for Chemotherapy," 27–32, Kräusslich et al., eds., *Curr. Comm. Mol. Biol.*, Cold Spring Harbor Laboratory Press (1989)). No cleavage (nor any alternative cleavage) was observed for AB 1, AB2 and ST2 (FIG. 8). The introduction of D-amino acid analogues in P2, P1 and P2' (peptides P2dT, C11, H10 and P2'dP) does not allow any cleavage of the modified substrates, which clearly indicates the stereochemical specificity of HRV2 2A (FIG. 7). CARBA substitution of the cleavage signal by ε-aminocaproic acid or shatin (peptides Capro and STAT) results in a complete loss of cleavability (FIG. 7).

Starting from the cleavage site VP 1–2A and the alternative site within 3D of the polio serotype 1 (Lee and Wimmer, *Virol.* 166:405–414 (1988)) it is possible to synthesise peptide substrates (P73 and P75) and the C-terminal cleavage products (P74 and P76) thereof.

Although there is an extreme difference between the primary sequence of the cleavage site of polio and rhino, the VP1-2A cleavage sequence of polio is accepted to a small extent by proteinase 2A. The alternative polio region in 3D (peptide 75) does not serve as a substrate for HRV2 2A (FIG. 8).

Chimeric peptide substrates consisting of an N-terminus of HRV1A, HRV1B, HRV39 or HRV49 (Palmenberg, A., in Molecular Aspects of Picornavirus Infection and Detection, Semler and Ehrenfeld, eds., Washington, D.C.: American Society for Microbiology, 211–231 (1988); Hughes et al., loc. cit. (1988)) and of a C-terminal region derived from HRV2 (Skern et al., loc. cit.) (FIG. 8; peptides RV1A, RV1B, RV39 and RV49), demonstrate the particular significance of the ITTA motif and/or the Arg in position P7.

Figure 4:
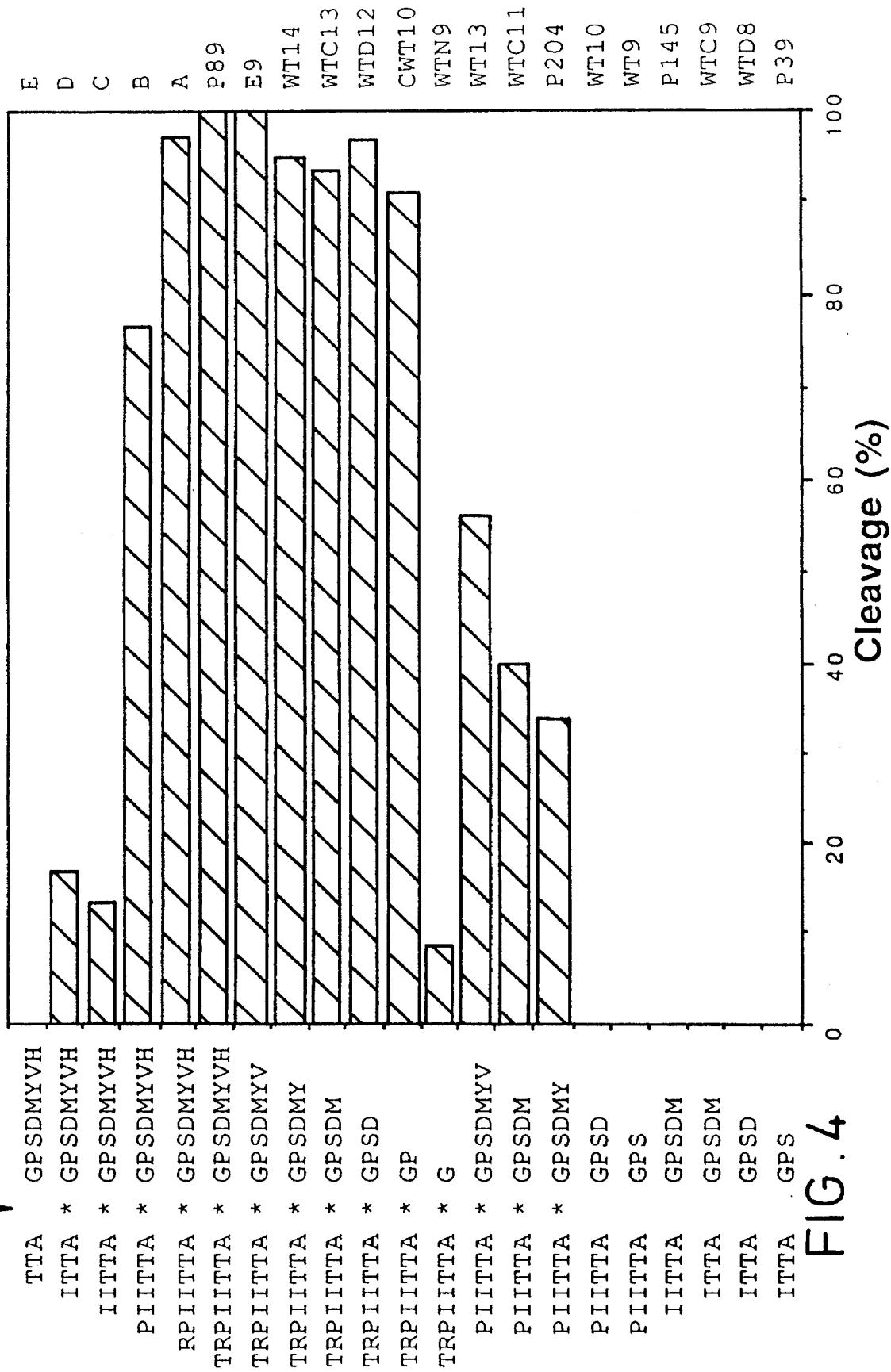
FIG. 4. Minimum length of Wild type substrates. The sequences of the peptide substrates used in this study are listed on the left. The asterisk indicates that the particular peptide substrate was cleaved at this position. The large arrow indicates the cleavage position expected. The efficiency of cleavability of each peptide is indicated as % cleavage compared with P89 (as given under the conditions in Example 7). The abbreviations for the peptides are shown on the right.

The peptides RV9, RV14, RV85 and RV89 (Leckie, G. W., loc. cit. (1988); Stanway et al., loc. cit. (1984); Callahan, loc. cit. (1985); Stanway, G., *J. Gen. Virol.* 71:2483–2501 (1990), and Duechler et at., loc. cit. (1987)) represent the Wild type cleavage site of the corresponding serotypes. The peptides RV9, RV14 and RV89, which have the greatest difference in the amino acid sequence (have neither an ITTA motif nor an Arg at position P7) cannot be cleaved at all; the peptides RV39, 1A and 1B can be cleaved by about 10% and the peptides RV85 and 49 can be cleaved with a high degree of efficiency (about 50%). This result shows once again that the N-terminal region of the peptides (especially the ITTA motif and/or the Arg in position P7) is crucial for cleaving. This was also demonstrated by the shortened Wild type peptides (FIG. 4).

Some P2-substituted peptides were coprecipitated with 2A, showing that these peptides are firmly bound to the proteinase 2A, possibly in the region of the active centre, but are not cleaved. The question then arises whether these or other peptides which are not clearable or only slightly cleavable are possible competitive inhibitors of P89.

The only peptides tested which behaved competitively were those which were derived either from shortened or deleted Wild type peptide substances (P145, WTD8 and AB2; FIG. 8) or those derived from peptides with "moderate" amino acid exchanges at position P1 (Ala for Asn; peptide G5) or P2 (Thr for Ser or Asn; peptides B4 and B8) (FIG. 6). Based on this knowledge and knowing that the ITTA motif or the Arg at position P7 plays a major part in the substrate interaction, the peptide inhibitors according to the invention may have, instead of the clearable Ala-Gly site, C4- or C6-acids, such as, for example, aminolerulinic acid, γ-aminobutyric acid or ornithine. These peptides would still be recognized as substrates but can no longer be cleaved because of the missing peptide bond. Based on their expected higher probability of staying in the active center of the enzyme, the peptides described should be effective as competitive inhibitors.

Another possibility is to replace the P1 and P2 group with γ-amino-β-hydroxybutyric acid. Some P1 and P2 peptide mutants (e.g. peptides G5, B4 and B8) have a modified IITFA motif which still permits efficient interaction with the proteinase but leads to a dramatically reduced cleavability and increases the likelihood of staying in the active center of the enzyme. The probably competitive mechanism of activity of the shortened and deleted peptides according to the invention (P145, WTD8 and AB2) is possibly also based on the fact that these peptides are indeed still recognized as a substrate by means of the ITFA motif but because of their shortness (P145 and WTD8) or the missing cleavage site (AB2), they cannot be cleaved. This obviously increases their likelihood of staying in the active center and therefore gives them the property of competitive inhibitors. A mutated peptide with an amino acid exchange Gly for Thr at position P1' was unable to be cleaved but demonstrated a certain inhibition showing that this amino acid position plays a minor role in the recognition of the substrate but is clearly sterically significant for the cleavage. The same is true of peptides which contain a CARBA substitution instead of the HRV2 cleavage signal Ala-Gly (FIG. 8; peptides Capro and STAT).

To sum up, the invention thus also includes peptides with an inhibitory effect on rhinoviral 2A proteinase derived from the amino acid motif TRPIITTAGPSDMYVH (SEQ ID NO:3), characterised in that they contain N- and/or C-terminal truncations and/or the ITTAGPS (SEQ ID NO:4) partial motif is altered.

The invention also includes those peptides which have additional chemical groups which are not normally part of this molecule. These "chemical derivatives" contain groups which improve the molecular solubility, the absorption, the biological half-life and so on or alternatively are capable of reducing the toxicity or undesirable side effects. Groups which mediate such effects are known (Remington's Pharmaceutical Sciences (1980)).

In particular, the invention includes peptides and chemical derivatives obtained therefrom which are derived, as described above, from the amino acid motif TRPIITTAGPS-DMYVH (SEQ ID NO:3), in which one or more amino acids are deleted and/or there is a moderate amino acid exchange at position P1 and/or position P2 and/or at position P2 an amino acid having a reactive side chain is incorporated and/or instead of the Ala-Gly cleavage site a C4 or C6 amino acid is incorporated and/or instead of the P1 and the P2 group α-amino-β-hydroxybutyric acid is incorporated.

Peptides with an abbreviated form of the above amino acid motif and an amino acid deletion at P1 and/or position P1' are preferred. These may be, for example, the peptides P145 (IITTAGPSDM) (SEQ ID NO:5), WTD8 (IITTAGPSD) (SEQ ID NO:6), or AB2 (TRPIITTPSD-MYVH) (SEQ ID NO:7).

The amino acid exchange at positions P 1 and P2 preferably comprises a moderate amino acid exchange, a moderate amino acid exchange being the exchange of one amino acid for another of similar size and charge distribution, e.g. the replacement of the amino acids of the original amino acid motif by Asn at position P2. Preferably, these may be the peptides G5 (TRPIITTNGPSDMYV) (SEQ ID NO:8), B4 (TRIITSAGPSDMYV) (SEQ ID NO:9), and B8 (TRPI-ITNAGPSDMYV) (SEQ ID NO: 10).

Moderate amino acid exchanges are for example:

| Original Residue | Exemplary Substitutions |
|---|---|
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Amino acids with a reactive side chain may be, for example, the amino acids α-aminobutyric acid, vinylglycine, homocysteine, homoserine, β-cyanoalanine, methylcysteine sulphoxide, etc.

The Ala-Gly cleavage site may for example be replaced by β-oeaminolaevulinic acid, α-aminobutyric acid or ornithine, γ-aminocaproic acid or statine.

Surprisingly, the invention also makes it possible to improve the affinity of peptide substrates of HRV2 2A. This is particularly true of the peptides which have methionine or tyrosine at position P1 instead of the amino acid alanine of the Wild type. These peptides can then serve as a starting point for preparing substrates with an increased affinity for HRV2 2A protease. The invention therefore also includes peptides with these substitutions for improving the substrate affinity.

The invention also includes pharmaceutical compositions for inhibiting HRV2A proteinase which contain the peptides described above, optionally with excipients and/or carriers and/or stabilisers known per se.

The invention also covers the use of the peptides described above in preparing pharmaceutical compositions for inhibiting HRV2A proteinase as well as a composition containing one of the above-mentioned peptides, optionally with excipients and/or carriers known per se, for inhibiting HRV2A proteinase. The invention also includes the use of the peptides described above for inhibiting HRV2A proteinase and a process for preparing the peptides by Fmoc strategy with activated esters or by HOBt/DIPCDI activation and by analogous methods.

The polypeptides according to the invention and the pharmacologically acceptable acid addition salts thereof may be converted in known manner into the usual formulations such as plain or coated tablets, pills, granules, aerosols, syrups, emulsions, suspensions and solutions using inert pharmaceutically suitable carriers or solvents. The proportion of pharmaceutically active compound(s) should be within the range from 0.5 to 90 wt.-% of the total composition, i.e. in amounts which are sufficient to achieve the dosage range specified hereinafter.

The formulations are prepared, for example, by diluting the active substances with solvents and/or carriers, optionally using emulsifiers and/or dispersing agents if water is used as a diluent, for example, organic solvents may be used as solubilising agents or auxiliary solvents.

The excipients used may be, for example, water, pharmaceutically acceptable organic solvents such as paraffins, vegetable oils, mono- or polyfunctional alcohols, carriers such as natural mineral powders, synthetic mineral powders, sugars, emulsifiers and lubricants.

The substances are administered in conventional manner, preferably by oral or parenteral route, more particularly on the tongue or intravenously. If taken orally the tablets may of course contain, in addition to the carriers mentioned above, additives such as sodium citrate, calcium carbonate and dicalcium phosphate together with various added substances such as starch, preferably potato starch, gelatine and the like. Furthermore, lubricants such as magnesium stearate, sodium laurylsulphate and talc may be used to produce the tablets. In the case of aqueous suspensions the active substances may be mixed with various flavour improvers or colourings in addition to the excipients listed above.

The tablets may also consist of a number of layers. Coated tablets may be prepared in the same way, by coating cores produced like the tablets with agents normally used for tablet coatings, such as collidone or shellac, gum arabic, talc, titanium dioxide or sugar. In order to obtain delayed release or avoid intolerance, the core may also consist of several layers. Similarly, the tablet coating may also consist of several layers, in order to obtain a delayed release, using the excipients mentioned for the tablets above.

Syrups of the active substances or combinations of active substances according to the invention may additionally contain a sweetener such as saccharin, cyelamate, glycerol or sugar as well as a flavoring improver, e.g. a flavoring such as vanillin or orange extract. They may also contain suspension adjuvants or thickeners such as sodium carboxymethylcellulose, wetting agents, e.g. condensation products of fatty alcohols with ethylene oxide or preservatives such as p-hydroxybenzoates.

Injectable solutions are prepared in the usual way, e.g. by adding preservatives such as p-hydroxybenzoates or stabilizers such as complexones and are packaged in injection vials or ampoules.

Capsules containing the active substances or combinations of active substances may, for example, be prepared by mixing the active substances with inert carriers such as lactose or sorbitol and packing them into gelatine capsules.

For parenteral use, solutions of the active substances may be prepared using suitable liquid carriers.

The dosage for oral use is 1 to 300 mg, preferably between 5 and 150 mg.

Nevertheless, it may be necessary to deviate from the amounts specified, depending on the body weight or the method of administration, the individual response to the drug, the type of formulation used and the time or length of time over which the drug is administered. Thus in some cases it may be sufficient to use less than the prescribed minimum whereas in other cases the upper limit may have to be exceeded. If larger quantities are administered it may be advisable to divide them into several smaller doses over the day. Furthermore, the polypeptides according to the invention or the acid addition salts thereof may also be combined with other kinds of active substance.

The present invention is described in further detail in the following non-limiting examples.

EXAMPLES

The following protocols and experimental details are referenced in the examples that follow:

Restriction enzymes and DNA modifying enzymes (New England Biolabs or Boehringer Mannheim) were used as recommended by the manufacturers. Plasmid DNA was prepared using the method of Birnboim and Doly (*Nucl. Acids Res.* 7:1513–1523 (1979)) and purified by gel filtration over Sephacryl S-1000. DNA fragments were separated by agarose gel electrophoresis and isolated over DE81-Cellulose paper (Maniatis et al., in: Molecular Cloning: A Laboratory Manual, Cold Spring Harbor Laboratory, Cold Spring Harbor, N.Y. (1982)). The sequencing was carried out according to Sanger et al. (*Proc. Natl. Acad. Sci. USA* 74:5463–5467 (1977)).

Oligopeptides were prepared using the fluoren-9-yl-methoxycarbonyl (Fmoc) strategy with activated esters or HOBt/DIPCDI activation on a Milligen Model 9050 peptide synthesiser or a Zinsser SMPS 350 peptide synthesiser. The solid phase used to bind the peptide acids was polydimethy-lacrylamide resin on kieselguhr (Pepsyn KA, Milligen/Biosearch), TentaGel S AC (Rapp polymer), Sasrin resin or Wang resin (Bachem, Switzerland) and for peptide amides TentaGel AM (Rapp polymer).

The Fmoc-coupled amino acid derivatives of the free and pentafluorophenylesters (Opfp esters) came from Bachem AG (Switzerland) and Novabiochem (Switzerland). The side chains were protected as follows: Arg (Mtr), Arg (Pmc), Asp (tBu), Cys (Trt), Glu (tBu), His (Boc), Ser (tBu) and Thr (tBu). The peptides were cleaved from the resin by HF treatment and the side groups were liberated by incubation for 3 hours in TFA/thioanisole/thiocresole (95:3:2, v/v). The complete removal of the Mtr protecting group was achieved by a one hours treatment with acid at 50° C. The peptides are dissolved in acetic acid, precipitated in diethylether, collected by centrifuging and lyophilised. The analytical HPLC (Waters System) was carried out on "Bakerbond wide pore C18" columns with a linear gradient $H_2O$/TFA (100:0.1) and acetonitrile/TFA (100:0.1). Semipreparative separation was carried out under the same conditions using a Hibar Lichsorb RP18 (Merck, Germany). The correct amino acid composition of all the peptides was investigated using plasma desorption mass spectroscopy on a BIG ION BIN K20.

Protease Inhibitors and Chemicals: Amastatin, Antipain, Bestatin, Chymostatin, E-64, Elastatinal, Epibestatin, Epiamastatin, Foroxymithin, Iodacetamide, Leupeptin, N-ethyl-maleimide, NLE-Sta-Ala-Sta, Pepslatin, Phosphoramidon, PMSF, TLCK and TPCK were obtained from Sigma. APMSF and 3,4-dichloro-isocumarin were obtained from Boehringer Mannheim. 1,10-phenanthrolene were obtained from Merck (Germany).

Example 1

Construction of an IPTG-inducible expression vector for active and inactive 2A proteinases in *E. coli* HB 101

The BstEII/HindIII fragment of pEx2A (Sommergruber et al., loc. cit. (1989)) which was deposited on Jul. 13, 1995, at the DSM under the terms of Budapest Treaty under accession number DSM 10110 which comprises the majority of the region coding for 2A with the exception of the first 11 N-terminal amino acids, is isolated and ligated with the following double stranded oligonucleotide (SEQ ID NO:1 and SEQ ID NO:2):

```
5'-  CATGGGCCCGAGTGACATGTATGTTCATGTAG       -3'
3'-      CCGGGCTCACTGTACATACAAGTACATCCAATG   -5',
```

The oligonucleotide comprises the missing N-terminal coding region of the proteinase 2A including a start codon. The oligonucleotides were prepared with an "Applied Biosystems DNA Synthesiser". Purification is carried out on OPC columns (McBride et al., *Biotechniques* 6:362–267 (1988)). The nucleotides are phosphorylated with T4 polynucleotide kinase. For the annealing process the complementary oligonucleotides are heated to 68° C. for 10 minutes and to 45° C. for 30 minutes; after cooling to an ambient temperature they are put on ice.

The 5' end of this oligonucleotide is a "sticky" NcoI cutting site whilst the 3' end is a "sticky" BstEII cutting site. The 5'-ATG triplet, being a start codon, is part of the NcoI recognition sequence which is used in order to clone the complete Met-2A coding region into the P PROK-1 expression vector linearized with NcoI and HindIII (CLONTECH Laboratories). The resulting vector makes it possible to express a mature proteinase 2A of HRV2 by IPTG induction (tac-promotor) in *E. coli* HB101 cells (ATCC No. 33694). A positive clone P PROK-½A-41 was designated 2A. In the same way, BstEII/HindIII fragments of pEx2A (Cys106:Ser) and pEx2A (ΔGly107/108) (Sommergruber et al., loc. cit. (1989)) are used to construct inactive 2A proteinases. The resulting vectors p PROK-½A (Cys106:Ser) and p PROK-½A (ΔGly107/108) were designated 9B and 1I, respectively.

Example 2

Figures 1, 1B:
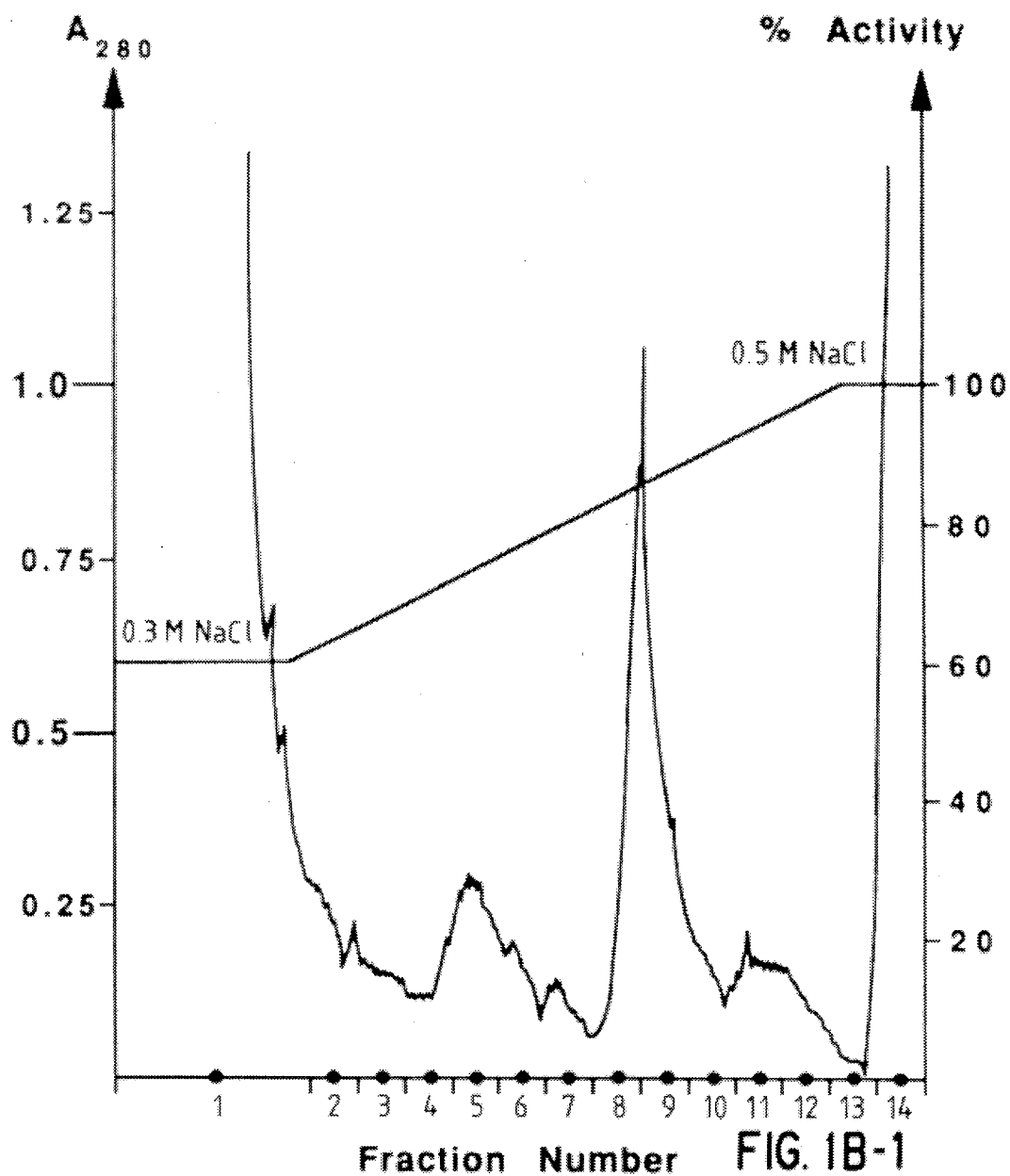
Figures 1, 1B, 2:
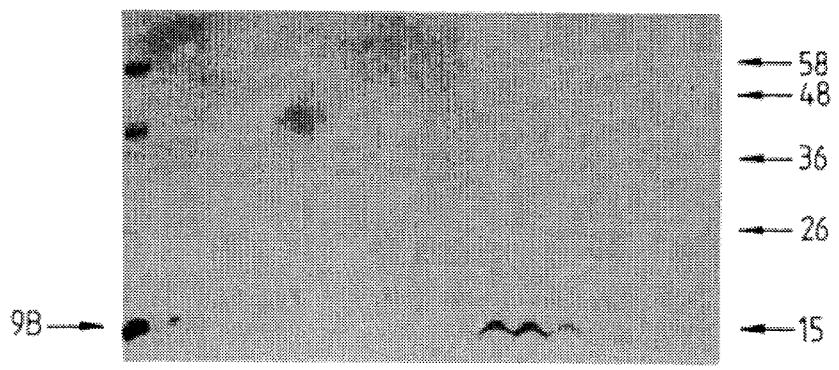
Figure 2:
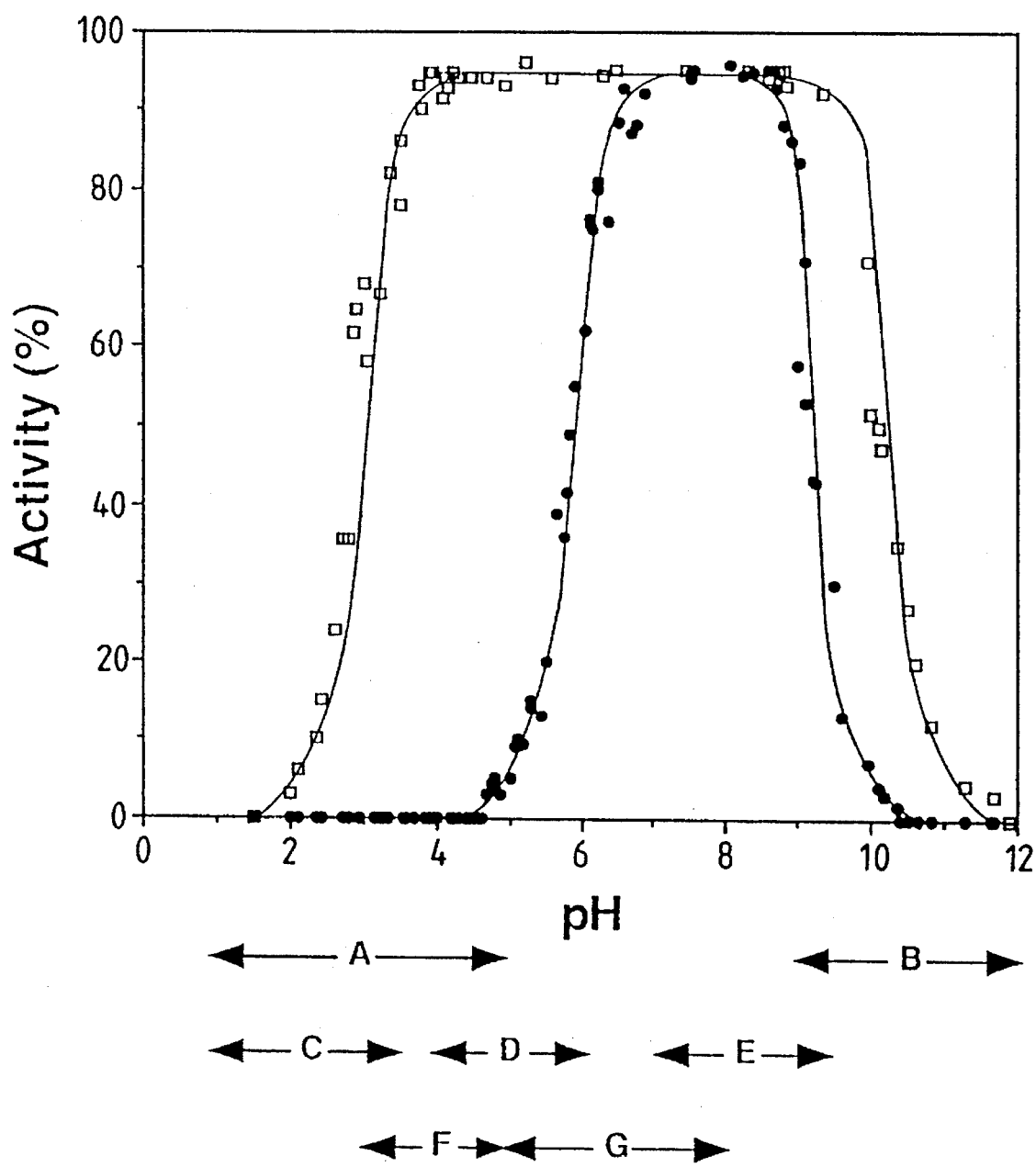

Expression of active and inactive 2A proteinase and purification by MONO Q-column chromatography 10 ml of preheated (35° C.) LB medium (+100 mg ampicillin/l) are inoculated with *E. coli* HB101 cells which contain either the expression vector for the active 2A p POK-½A-41 or for the inactive proteinase 2A p PROK-⅑B and p PROK-⅑ and incubated in an incubation shaker at 35° C. for 8 hours ($OD_{600}$:1.75). After dilution by the addition of 10 ml of culture liquid to 90 ml of LB medium preheated to ambient temperature (+100 mg of ampicillin per liter) the culture is incubated for 2 hours ($OD_{600}$:1.10), induced with IPTG (final concentration 0.5 mM) and incubated for 13 hours ($OD_{600}$:2.2). After this procedure there is a maximum of proteinase 2A present in soluble form (about 15 to 20% of the total quantity of 2A). The culture liquid is centrifuged (10 min, 4000 g, 4° C.) and the cell pellet from 50 ml of culture liquid is resuspended in 18 ml of ice cold 50 mM Tris-HCl (pH 8.5) and 5 mM DTT. The cells are broken up by treating with ultrasound three times for 20 seconds each time (18 ml aliquots in "Corning tubes" whilst cooling with ice with an "MSE ultrasonic power" apparatus). To avoid overheating, a gap of 20 seconds is left between the individual ultrasound treatments. In order to separate off any insoluble material the material is centrifuged first in a Sorvall centrifuge (5 min 5000 g, 4° C.) and subsequently in a Beckman ultracentrifuge, Ti50 Rotor (30 min 35000 g, 4° C.). The supernatant is placed on a MONO Q 5/5 column and eluted by means of a 30% to 50% NaCl saline gradient (elution buffer A: 5 mM Tris-HCl (pH 8.5), 5 mM DTT; elution buffer B: 50 mM Tris-HCl (pH 8.5), 5 mM DTT and 1M NaCl). Fractions containing active proteinase 2A are identified by correct cleaving of the peptide substrate "P89" (16-mer, Example 3), which represents the Wild type cleavage sequence of HRV2 2A proteinase (Sommergruber et al. loc. cit. (1989)). The main activity is eluted at about 45% of the NaCl gradient. In addition, dot blots may be made in order to identify the fractions containing 2A. The identification of inactive 2A proteinase by means of Western blots in MONO Q fractions is carried out according to Sommergruber et al., loc. cit. (1989) (FIGS. 1A and 1B). The fractions containing 2A are combined and adjusted to 8% glycerol (Sigma, "molecular biology grade") and 1 mg/ml of acetylated BSA (Biolabs). In siliconized Eppendorf vessels 0.5 ml aliquots are frozen in liquid nitrogen and stored at −20° C. The activity of the 2A is maintained for some months. Thawing results in a 5 to 10% loss of activity.

The expression product of 2A, 9B and 1I were isolated using this procedure. FIG. 1 shows typical MONO Q elution profiles for the separation of the 2A and 9B extracts. The mutant 1 I shows an elution profile identical to 9B. The correct N-terminal sequence of the fractions containing 2A was demonstrated by N-terminal sequencing (SEQ ID NO:11 and SEQ ID NO:12).

Met(formyl—Met?)—(Gly)—Pro—Ser—(Asp)—Met—Tyr—

—Val—$X_{His}$—Val—$X_{Gly}$—$X_{Asn}$—Leu—Ile—$X_{Tyr}$—

The blocking of a majority of material for the N-terminal sequencing makes it clear that the overwhelming majority of the 2A material has a formylated N-terminal methionine.

Example 3

Trans-cleavage assay: Kinetics of peptide cleavage by means of pantally pufffled proteinase 2A 100 μl of the MONO Q fractions which contain active proteinase 2A, or 100 μl of the stabilised parent solutions, were mixed with 5 μl of an aqueous peptide solution (4 or 2 mg/ml) and incubated at 34° C. for 2, 4, 8, 16 and 32 minutes. For competitive or inhibitory studies, an additional 5 μl of solution containing the substance for competition or inhibition are added. The reaction is stopped by adding an equal volume of a 0.5M $HClO_4$ solution. The samples are cooled to 0° C. for 10 minutes or frozen overnight at −20° C. After centrifugation (Eppendorf centrifuge, 10 min, 4° C.) an equal volume of a 1.4M $K_2HPO_4$ solution is added. The samples are left to stand for 5 minutes at ambient temperature and the precipitate is separated off by centrifuging. The supernatant is added to a reverse phase HPLC column and the peptides are separated either by means of a short gradient (Merck Supersphere C18 column) or a long gradient (Bakerbond WP C18 column) with aqueous 0.1% trifluoroacetic acid and acetonitrile as the mobile phase. The reaction products are detected by UV absorption at 214 and 280 nm. The course of the reaction over a period of time (% cleavage of the peptide substrate) is determined by "reverse phase" HPLC. The area of the newly formed peptide peak corresponding to the quantity of the carboxy- and amino terminal cleavage products is determined for each case and compared with the area of the uncleaved P89. The cleavage products are determined either by comigration with the corresponding reference peptides and amino acid analysis or by protein sequencing (Hunkapillar and Hood, 1983, loc. cit.).

As described in Example 2 the active proteinase 2A is identified by means of a 16 amino acid long Wild type oligopeptide substrate "P89" (acetyl-TRPIITTA*GPSDMYVH-$NH_2$) (SEQ ID NO:3) which is specifically cleaved after the amino acid pair Ala-Gly (FIG. 1A), whereas neither the Cys106:Ser mutant 9B nor the ΔGly107/108 mutant 1I brings about specific cleaving of the peptide substrate P89 (FIG. 1B). Because of the presence of endogenous proteinases in E. coli, a small non-specific cleaving of P89 is usually observed between Ile-Ile and/or Arg-Pro in unpurified extracts. After purification with MONO Q columns this non-specific cleaving activity is clearly separated from 2A-containing fractions (non-specific cleaving is detected only in the MONO Q fractions 1 to 3; FIG. 1). Moreover, no background activity (specific or non-specific) is found in fractions which contain the expression product of 9B (FIG. 1B) or 1I. In all other studies these partially purified 9B and 1I fractions serve as negative controls. The use of a plurality of different peptide substrates shows that no cleaving (specific or non-specific) takes place in partially purified 9B or 1I extracts. These data make it possible to rule out any simultaneous purification of interfering E. coli proteinases.

Example 4

Influence of the pH value on the proteolytic trans-activity

100 μl of freshly prepared, non-stabilized, 2A-containing MONO Q fractions (25 mM Tris-HCl (pH 8.5), 5 mM DTT, 450 mM NaCl) as well as frozen, stabilized aliquots (25 mM Tris-HCl (pH 8.5), 5 mM DTT, 450 mM NaCl, 8 % glycerol and 1 mg/ml acetylated BSA) were adjusted to different pH levels by the addition of 10 μl of a 0.5M solution of various buffer solutions (FIG. 2). To avoid any inhibitory effect of the buffers selected and to exclude any effects resulting from the different ion intensity of a buffer system, various buffer systems are used: glycine/HCl, glycine/NaOH, sodium citrate/HCl, phthalic acid/NaOH, Tris/HCl, $NaH_2PO_4$/$Na_2HPO_4$ and $CH_3COOH$/NaOH. After 10 minutes' incubation at ambient temperature the pH is measured with a microelectrode (Ingold) and kinetic studies are carried out as described in Example 3. For the proteinase 2A there is an optimum pH at between 7 and 8.5.

In order to investigate the stability of this enzyme the proteinase 2A is pre-incubated at varying pH levels for 20 minutes at ambient temperature, followed by adjustment of the pH to between 8 and 8.5 by the addition of 1/20 volume of a 2M Tris-HCl solution (pH 8.5). The trans-cleavage assay was then carried out. By comparison with the first test, 2A shows a greater tolerance at acid pH levels, whereas smaller variations in the basic range lead to greater sensitivity (FIG. 2). The drawing in FIG. 2 shows that the proteinase 2A is not irreversibly destroyed at lower pH levels; when retitration occurs from pH levels of between 4 and 9 to pH 8.5, it re-acquires its full activity. Since this curve represents the stability of the proteinase 2A, obviously kinetically important ionisations occur at acidic rather than at basic side groups.

Example 5

Determining the Km value when using the peptide substrate P89

In order to identify the optimum temperature a set of trans-cleavage assays are carried out. Samples containing the proteinase 2A are incubated for 10 minutes at the desired temperature before kinetic investigations. Furthermore, the temperature range within which 20% of the cleavage shows a linear curve within the first 5 to 10 minutes is identified. The initial increase thus identified is used for determining Km with P89 as substrate. The temperature curve shows a linear range in proteolytic activity between 5° C. and 20° C., followed by a plateau at 20° C. to 35° C. and a sharp fall at 37° C. The suitable measuring range with a linear curve is found to be at 15° C.

In order to identify the Km value for the Wild type substrate P89 a set of trans-cleavage assays are carried out at 15° C. with various P89 substrate concentrations (between 50 and 500 μmol/l). Samples are taken at half minute intervals up to a total duration of 3 minutes. For each substrate concentration the reaction speed was determined (% cleavage of P89). The experiment is repeated three times with various 2A preparations. A Km-value of $(5.4 \pm 0.02) \times 10^{-4}$ mol/l is obtained.

Example 6

Effect of known proteinase inhibitors on the cleaving of peptide P89

The effect of a series of known inhibitors of serine, cysteine, aspartate and metalloproteinases as well as the effect of reducing agents on the activity of 2A relative to peptide P89 is investigated. The trans-cleavage assays are carried out as described, except that the various proteinase inhibitors are added before the start of the reaction. The kinetic investigations which were carried out with freshly prepared and stabilized 2A preparations and repeated three times, show a high degree of reproducibility. The results are shown in FIG. 5. If DMSO, methanol or ethanol are required to dissolve the inhibitors, they are also added to the controls in corresponding amounts. Moreover, in order to investigate SH-sensitive inhibitors, dialysed 2A preparations are used (dialysed against 50 mM Tris-HCl, pH 8.5, and 400 mM NaCl). The conditions used here and effective concentrations of the inhibitors are as described (Beynon and Salvesen, loc. cit. (1989)).

Example 7

Role of the peptide length for 2A

A number of peptides are synthesized in order to determine the minimum peptide length for cleaving by the HRV2 proteinase 2A. It is shown that a 16 amino acid long peptide (P89) which comprises the region between the C-terminus of VP1 and the amino terminus of 2A can serve as an effective substrate for the proteinase 2A (Sommergruber et al., loc. cit. (1989)). The ability of shorter peptide to act as substrate is investigated by trans-cleavage assays (under identical conditions to those described in Example 3) and compared with P89. All the peptides in this investigation contain acetylated N- and amidated C-termini. The results are shown in FIG. 4. Successive C-terminal deletions within P89 (peptides E9, WT14, WTC13, WTD12, CWT10 and WTN9) have far less influence on the clearability than N-terminal deletions (peptides A, B, C, D and E). Reductions in the lengths of the amino terminal end of P89 by the amino acid proline (position P6) results in a fall in cleavability of one order of magnitude. Obviously, this part of the peptide is critical for effective recognition and cleaving (peptides C and D). By contrast, however, the minimum number of one amino acid (peptide WTN9) on the carboxy terminal end is sufficient for 10% cleaving. Consequently, the C-terminal end plays a smaller role in the substrate recognition and/or cleaving. The degradation of both ends of the peptide substrate results in an 11-mer substrate (WTC11) which can still be efficiently cleaved (40%). Further degradation of both ends does not permit any further cleaving. A change in solubility has never been observed to be the cause of differences in clearability under the test conditions used.

Example 8

Intermolecular substrate specifidty of synthetic peptide substrates and inhibition of P89 cleaving by modified peptide substrates.

Rhinoviral 2A proteinases recognize an Ala or Val at position P1 and a Gly at a position P1', with the exception of the proteinase 2A or HRV14, which cleaves a Tyr-Gly bond, as in the serotypes of poliovirus. Coxsackie viruses have a Thr-Gly cleavage sequence at their VP1-2A cutting site. The majority of cleavage sequences of the rhino- and enteroviruses have a Thr at position P2 and/or P3. Only HRV14 and HRV9 (Kräusslich and Wimmer, loc. cit. (1988)) have no Thr at one of these positions (Stanway et al., loc. cit. (1983); Lecki, G. W., loc. cit. (1988)). Furthermore, all known rhinovirus strains have a proline at position P2' with the exception of HRV14. In order to understand more about the different distribution of the amino acids for the substrate specificity of the transactivity of 2A, a set of 15-mer peptides are synthesized which have individual mutations at positions P2, P1, P1 ', P2' and P3' (FIG. 4). The original length of P89 (16 amino acids) is reduced (15 amino acids), because this permits better separation of the various peptide substrates and their cleavage products on the small HPLC gradient and according to the present data on the shortening of the peptide substrates it has no influence on the kinetics of proteolysis.

With these modified peptide substrates, trans-cleavage assays are carried out as described. In order to allow comparison of the efficiency of cleaving of the mutated peptides, a 15-mer Wild-type substrate (E9, FIG. 6–9 is synthesized, which is cleaved just as efficiently as the 16-mer Wild-type substrate P89 (FIGS. 4 and 6–8). In order to rule out any non-physiological influence of the charge which occurs as a result of free N- or C-terminal amino acids, some of the Wild-type substrates including P89 are acetylated at their N-termini and carboxylated at their C-termini (indicated by an open triangle in FIG. 4). This applies particularly to the charge distribution of smaller peptides of less than 10 amino acids. However, for peptides with a length of 15 and 16 amino acids, it is found that they show no significant difference in cleavability, irrespective of whether they are acetylated and amidated. This modification is omitted in subsequent tests. In cases where cleaving is observed, the cleavage sites occurring are determined by N-terminal amino acid sequencing or by comigration with corresponding reference peptides. The mutation analyses show high tolerance for exchanges at positions P1, P2' and P3 ', but an absolute dependency on threonine at P2 and glycine at P1' (FIGS. 6 and 7). HRV2 2A at position P2 tolerates only exchanges of amino acids which come closest to Thr in their size and polarity (peptides B4, B8 and B12; FIG. 6). Positively charged groups in position P2 (peptides C3 and C5) show a degree of cleavability (albeit greatly reduced). One possible interpretation of the acceptance of positive charges at this position would be the structural similarity to trypsin-like proteinases (Bazan and Fletteriek, 1990, loc. cit.), which, as is well known, cleave after basic amino acids. All other mutations in the peptide substrate mean that the peptide can no longer be cleaved by 2A (FIG. 6). Position P2 therefore seems to play an essential part (in addition to the ITTA-motif and the Arg in the position P7).

By comparing the percentage clearability of the peptide mutants at a moment where there is 50% cleaving of the Wild-type substrate (P89 and E9), it was possible to show that there is a higher efficiency of clearability in the presence of a Met or Tyr in position P1 (peptides F10, H2, P146 and F) (FIG. 6). These two groups in P1 would appear to create a kinetically more favorable situation for the trans-activity for HRV2 2A.

Furthermore, deletions are inserted in the Wild-type substrate (peptides AB1, AB2 and ST2) in order to check whether the HRV2 2A also accepts other less dominant cleavage signals within a peptide, as described for the cis activity of polio 2A (Hellen et al., loc. cit. (1989)). No cleaving (nor any alternative) is observed for AB1, AB2 and ST2 (FIG. 8). The introduction of D-amino acid analogues at P2, P1 and P2' (peptides P2dT, C11, H10 and P2'dP) allowed no cleaving of the modified substrates, which is a clear indication of the stereochemical specificity of HRV2 2A (FIG. 7). A CARBA-substitution of the cleavage signal by ε-aminocaproic acid or statin (peptides Capro and STAT) resulted in a total loss of cleavability (FIG. 7).

Starting from the cleavage site VP1-2A and the alternative site within 3D of the polioserotype 1 (Lee and Wimmer, loc. cit. (1988)) peptide substrates (P73 and 75) and their C-terminal cleavage products (P74 and P76) were synthesized.

Although there is an extreme difference here between the primary sequence of the cleavage site of polio and rhino, the VP1–2A cleavage sequence of polio is accepted by HRV2 2A proteinase to a small extent, indicating a structural similarity, albeit minimal, between P89 and P73. The alternative polio region in 3D (peptide 75) does not serve as a substrate for HRV2 2A (FIG. 8).

Chimeric peptide substrates consisting of an N-terminus of HRV1A, HRV1B, HRV39 or HRV49 (Palmenberg, A., in Molecular Aspects of Picornavirus Infection and Detection, Semler and Ehrenfeld, eds., Washington, D.C., American Society for Microbiology, 211–231 (1988); Hughes et al., loc. cit.) and of a C-terminal region derived from HRV2 (Skern et al., loc. cit.) (FIG. 8; peptides RV1A, RV1B, RV39 and RV49), show the particular importance of the ITTA motif and/or of the Arg in position P7. The peptides RV9, RV14, RV85 and RV89 (Lecki, G. W., loc. cit. (1988); Stanway et al., loc. cit. (1984); Callahan, loc. cit. (1985); Stanway, G., loc. cit. (1990) and Duechler et al., loc. cit.) represent the Wild type cleavage site of the corresponding serotypes. The peptides RV9, RV14 and RV18 which have the greatest difference in amino acid sequence (there is neither an ITTA motif nor an Arg at position P7) cannot be cleaved at all; the peptides RV39, 1A and 1B can be cleaved with about 10% efficiency compared with P89 and peptides RV85 and 49 can be cleaved with good efficiency (about 50%). This result shows once again that the N-terminal region of the peptides (particularly the ITTA motif and/or the Arg in position P7) is crucial for cleaving. This was also shown by the shortened Wild type peptides (FIG. 4).

Some P2-substituted peptides were coprecipitated with 2A, showing that these peptides are firmly bound to the proteinase 2A, possibly in the region of the active centre, but are not cleaved. The question then arises as to whether these or other peptides which are non-clearable or only slightly cleavable are competitive inhibitors of P89. From the ability of non-cleavable or only slightly cleavable peptides to act as competitive inhibitors it is also possible to infer whether an amino acid of the peptide substrate is involved in the substrate binding or interacts directly with the catalytic center of the 2A. In order to increase the concentration of the different peptide substrates, aliquots of the parent solution (4 mg or 2 mg/ml) were lyophilized and the pellets were dissolved directly in the corresponding volume of the samples containing the 2A. The only peptides tested which became competitive were those which were derived either from shortened or deleted Wild type peptide substrates (P145, WTD8 and AB2; FIG. 8) or from peptides with "moderate" amino acid exchanges at position P1 or P2 (Ala for Asn, peptide G5, or Thr for Ser or Asn, peptides B4 and B8). A mutated peptide with an amino acid exchange Gly for Thr at position P1' could not to be cleaved but showed a clear, albeit small inhibition, indicating that this amino acid position plays a minor part in the substrate recognition but is obviously sterically important for the cleaving. The same is true of peptides which contain a CABRA substitution instead of the HRV2-cleavage signal Ala-Gly (FIG. 8; peptides Capro and STAT).

Example 9

Cleavage assays for determining the $(V_{max}/K_m)_{rel}$ value

The cleavage assays were carried out as described above with a mixture of the standard peptide P89 and the test peptide in question (100 μm in each ease). Aliquots were taken at half minute intervals up to 4 minutes and then after 8, 16 and 32 minutes and treated as described above. The peptides were analyzed by HPLC as described above. Analysis of the peak areas obtained made it possible to determine the extent of substrate conversion. The data obtained were evaluated as described by Pallai et al. (*J. Biol. Chem.* 264:9738–9741 (1989)) in order to determine the $(V_{max}/K_m)_{rel}$ values. The value derived for substrates 1 and 2 using $$(V_{max}/K_m)_1/(V_{max}/K_m)_2 = \log(1-F_1)/\log(1-F_2)$$

where F is the converted substrate fraction. In all the competitive assays carried out the substrate and product peptides were separable from one another. All the peptides from which no products were obtained within 32 minutes were incubated with HRV2 2A for a total of 3 hours. If no products were obtained after this period the substrates were defined as "not cleaved".

The $(V_{max}/K_m)_{rel}$ values are shown in FIGS. 9 to 11.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A DNA comprising a DNA vector fragment which is:
   (a) NcoI/HindIII linearized pPROK-1 comprising a tac promoter, and
   (b) a DNA segment encoding an HRV proteinase 2A which is operably linked to said tac promoter, wherein said DNA is capable of expressing mature, soluble, enzymatically active HRV proteinase 2A when present in *E. coli;* wherein 15% to 20% of the total amount of HRV proteinase 2A is present in soluble form when expressed in said *E. coli,* and wherein said DNA vector is pPROK-½A-41.

2. An *E. coli* cell that contains the DNA molecule according to claim 1.

* * * * *